US011883447B2

(12) United States Patent
Trajkovski et al.

(10) Patent No.: US 11,883,447 B2
(45) Date of Patent: Jan. 30, 2024

(54) METHODS AND PROBIOTIC COMPOSITIONS FOR THE TREATMENT OF METABOLIC DISEASES AND DISORDERS

(71) Applicant: Research Development Foundation, Carson City, NV (US)

(72) Inventors: Mirko Trajkovski, Geneva (CH); Claire Chevalier, Geneva (CH); Melis Çolakoğlu, Geneva (CH)

(73) Assignee: Research Development Foundation, Carson City, NV (US)

( * ) Notice: Subject to any disclaimer, the term of this patent is extended or adjusted under 35 U.S.C. 154(b) by 451 days.

(21) Appl. No.: 17/025,811

(22) Filed: Sep. 18, 2020

(65) Prior Publication Data

US 2021/0077549 A1    Mar. 18, 2021

Related U.S. Application Data

(60) Provisional application No. 63/069,458, filed on Aug. 24, 2020, provisional application No. 62/902,076, filed on Sep. 18, 2019.

(51) Int. Cl.
*A61K 35/747* (2015.01)
*C12N 1/20* (2006.01)
*A61P 3/00* (2006.01)

(52) U.S. Cl.
CPC .............. *A61K 35/747* (2013.01); *A61P 3/00* (2018.01); *C12N 1/20* (2013.01)

(58) Field of Classification Search
None
See application file for complete search history.

(56) References Cited

U.S. PATENT DOCUMENTS

| 9,039,966 | B2 | 5/2015 | Anderson et al. | |
| 9,956,255 | B1 * | 5/2018 | Ko | A61P 3/04 |
| 10,086,019 | B1 | 10/2018 | Ko et al. | |
| 10,111,915 | B1 | 10/2018 | Ko et al. | |
| 2007/0031451 | A1 | 2/2007 | Slifka et al. | |

FOREIGN PATENT DOCUMENTS

| WO | WO2013/173466 | | 11/2013 | | |
| WO | WO-2017079450 A1 | * | 5/2017 | ............. | A61K 35/74 |
| WO | WO2019/051380 | | 3/2019 | | |
| WO | WO-2019072205 A1 | * | 4/2019 | ............... | A61L 2/10 |
| WO | WO2020/069282 | | 4/2020 | | |

OTHER PUBLICATIONS

American Type Culture Collection, "Parabacteroides goldsteinii BAA-1180™" product sheet; ATCC: Manassas, VA,; pp. 1-5 (Year: 2021).*
BacDive, "Parabacteroides goldsteinii DSM 19448, ATCC BA 1180, CCUG 48944, JCM 13446, KCTC 15612, WAL 12034"; https://bacdive.dsmz.de/strain/12500; accessed Mar. 24, 2023 (Year: 2023).*
Liu et al. "Physical activity differentially affects the cecal microbiota of ovariectomized female rats selectively bred for high and low aerobic capacity", PLOS ONE, vol. 10, article e0136150, pp. 1-17. (Year: 2015).*
Ramos-Molina et al., "Dietary and Gut Microbiota Polyamines in Obesity- and Age-Related Diseases", Frontiers in Nutrition, vol. 6, article 24, pp. 1-15 (Year: 2019).*
Sadasivan et al., "Exogenous administration of spermine improves glucose utilization and decreases bodyweight in mice", European Journal of Pharmacology, vol. 729, pp. 94-99 (Year: 2014).*
Aponte et al., "Therapeutic, Prophylactic, and Functional Use of Probiotics: a Current Perspective", vol. 11, Article 562048, (Sep. 2020), Frontiers in Microbiology.
Calinescu et al., "Carboxymethyl high amylose starch (CM-HAS) as excipient for *Escherichia coli* oral formulations", Eur J Pharm Biopharm, 60(1):53-60, 2005.
Cani, "A bacteria likely to reduce the cardiovascular risks of 1 in 2 people", UCLouvain Press Release, Jul. 1, 2019.
Cani, "Human gut mierobiome: hopes, threats and promises", Gut, 67:1716-1725, (2018).
Chelakkot et al., "Akkermansia muciniphila-derived extracellular vesicles influence gut permeability through the regulation of tight junctions," *Experimental & Molecular Medicine* vol. 50, p. e450, 2018.
Choi et al., "Gut microbe-derived extracellular vesicles induce insulin resistance, thereby impairing glucose metabolism in skeletal muscle," *Sci Rep*, 5: 15878, 2015.
Cohut, "Even 'dead,' this probiotic may be effective against inflammation", MedicalNewsToday, downloaded from the world wide web at medicalnewstoday.com/articles/327276 on Oct. 13, 2022, published Dec. 10, 2019.

(Continued)

*Primary Examiner* — Michelle F. Paguio Frising
(74) *Attorney, Agent, or Firm* — Parker Highlander PLLC

(57) ABSTRACT

Disclosed are methods and probiotic compositions for the treatment of a metabolic disease or disorder such as, e.g., obesity, type 2 diabetes, or fatty liver. In some embodiments, heat-inactivated *Parabacteroides goldsteinii* is enterically administered to a subject, such as a human patient, to treat the metabolic disease or disorder or to promote the development of warm microbiota to treat the metabolic disease or disorder. In some aspects, spermine or spermidine may be administered to a subject or used in vitro to promote the growth of microbiota that can be used for the treatment of a metabolic disease or disorder.

37 Claims, 17 Drawing Sheets

(56) References Cited

OTHER PUBLICATIONS

Dar et al., "Lactobacillus acidophilus inhibits bone loss and increases bone heterogeneity in osteoporotic mice via modulating Treg-Th17 cell balance", Bone Rep. Feb. 5, 2018;8:46-56.
Davis, "The Gut Microbiome and Its Role in Obesity", Nutr Today. Jul.-Aug. 2016;51(4):167-174.
Erttmann et al., "Hydrogen peroxide release by bacteria suppresses inflammasome-dependent innate immunity", Nat Commun 10:3493, 2019.
Govander et al., A Review of the Advancements in Probiotic Delivery: Conventional vs. Non-conventional Formulations for Intestinal Flora Supplementation, AAPS PharmSciTech, 15(1):29-43, 2014.
Grigoryan et al., "Inactivation Kinetics of *Escherichia coli* and *Staphylococcus Aureus* by a Hydrogen Peroxide Based Disinfectant",*Journal of Hygienic Engineering and Design*, UDC 579.67:8-11, (2018).
Hussan et al., "A Review of Recent Advances of Interic Coating", Journal of Pharmacy 2(6):5-11, 2012.
Igarashi et al., "Modulation of cellular function oby polyamines", Int J Biochem Cell Biol., 42(1):39-51, 2010.
International Search Report and Written Opinion for PCT/US2020/051581 dated Feb. 12, 2021, 13 pages.
Kaiyala et al., "Acutely Decreased Thermoregulatory Energy Expenditure or Decreased Activity Energy Expenditure Both Acutely Reduce Food Intake in Mice", PLoS ONE 7(8):e41473, (2012).
Lee et al., "The Effect of Lactobacillus gasseri BNR17 on Postmenopausal Symptoms in Ovariectomized Rats", J Microbiol Biotechnol. Sep. 28, 2021;31(9):1281-1287.
Lin et al., "Effects of bacterial inactivation methods on downstream proteomic analysis", Microbiol Methods, 112:3-10, 2015.
MacLean et al., "Inactivation of bacterial pathogens following exposure to light from a 405-nanometer light-emitting diode array", Appl Environ Microbiol, 75(7):1932-7, 2009.
Malik, et al., "The inactivation of bacillus subtilis spores at low concentrations of hydrogen peroxide vapor.", J. Food Eng., 114(3):391-396, 2013.
Manas, et al., "Microbial inactivation by new technologies of food preservation", *Journal of Applied Microbiology* 98:1387-1399, 2005.
Meyer et al., "Body Temperature Measurements for Metabolic Phenotyping in Mice", Frontiers in Physiology, 8, 2017.
Million et al., "Obesity-associated gut microbiota is enriched in Lactobacillus reuteri and depleted in Bifidobacterium animalis and Methanobrevibacter smithii", Int J Obes 36, 817-825 (2012).
Morrison et al., "Brain polyamine levels are altered in Alzheimer's disease", *Neurosci Lett.*, 197(1):5-8, 1995.
Nilsson et al., "Lactobacillus reuteri reduces bone loss in older women with low bone mineral density: a randomized, placebo-controlled, double-blind, clinical trial", J Intern Med. Sep. 2018;284(3):307-317.
Soda et al., "Spermine, a Natural Polyamine, Supresses LFA-1 Expression on Human Lymphocyte", *J Immunol.*, 175(1):237-45, 2005.
Tian et al., "Inactivation of *Staphylococcus aureus* and Enterococcus faecalis by a direct-current, cold atmospheric-pressure air plasma microjet", J Biomed Res. Jul. 2010;24(4):264-9.
Turchanowa et al., "Influence of physical exercise on polyamine synthesis in the rat skeletal muscle",*Eur J Clin Invest*. 30(1):72-8, 2000.
Wu et al., "Gut commensal Parabacteroides goldsteinii plays a predominant role in the anti-obesity effects of polysaccharides isolated from Hirsutella sinensis", Hirsutella sinensis, Gut. 68(2):248-262, 2019.
Yamamoto et al., "The Natural polyamines spermidine and spermine prevent bone loss through preferential disruption of osteoclastic activation in ovariectomized mice", *Br J Pharmacol.*, 166(3):1084-1096, 2012.
Yang et al., "Colon-specific drug delivery : new approaches and in vitro/in vivo evaluation", International Journal of Pharmaceutics, 235(1-2):1-15, 2002.
Terpou et al., "Probiotics in Food Systems: Significance and Emerging Strategies Toward Improved Viability and Delivery of Enhanced Beneficial Value", *Nutrients*, 11, 1591, 2019.
Aguilar-Toalá et al., "Postbiotics: an evolving term within the functional foods field", *Trends in Food Science & Technology*, 75:105-114, 2018.
Araya, et al., "Food and Agriculture Organization of the United Nations, Health and Nutritional Properties of Probiotics in Food including Powder Milk with Live Lactic Acid Bacteria", Report of a Joint FAO/Who Expert Consultation, American Cordoba Park Hotel, Cordoba, Argentina Oct. 1-4, 2001.
Fernandez et al., "Autophagy counteracts weight gain, lipotoxicity and pancreatic pbeta]-cell death upon hypercaloric pro-diabetic regimens", *Cell Death & Disease*, 8(8):e2970-e2970, 2017.
Supplementary European Search Report for EP Application No. 20865610 dated Sep. 6, 2023, 10 pages.

\* cited by examiner

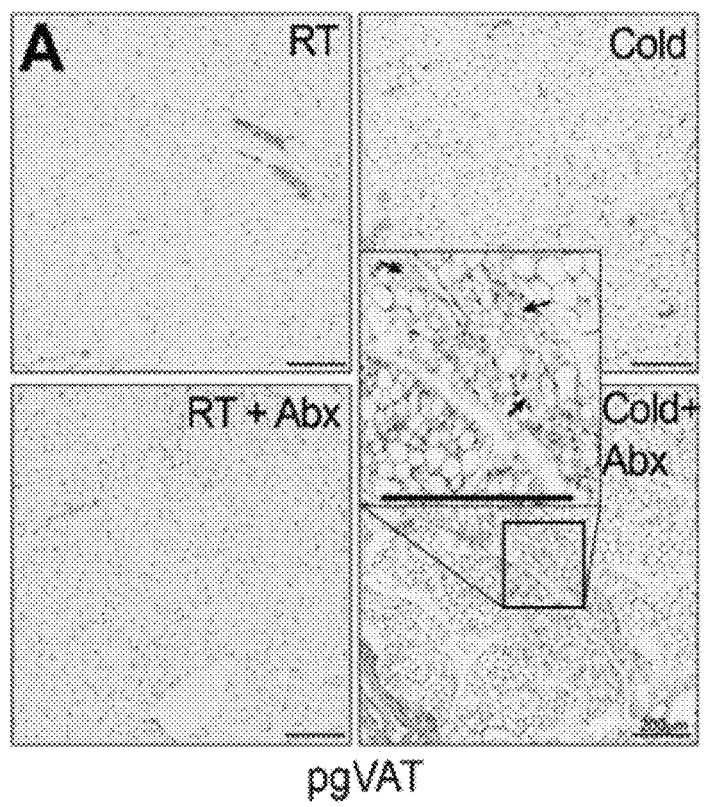
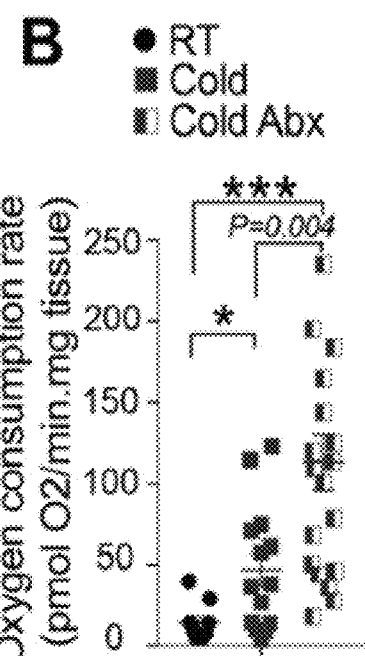
FIGS. 7A-B

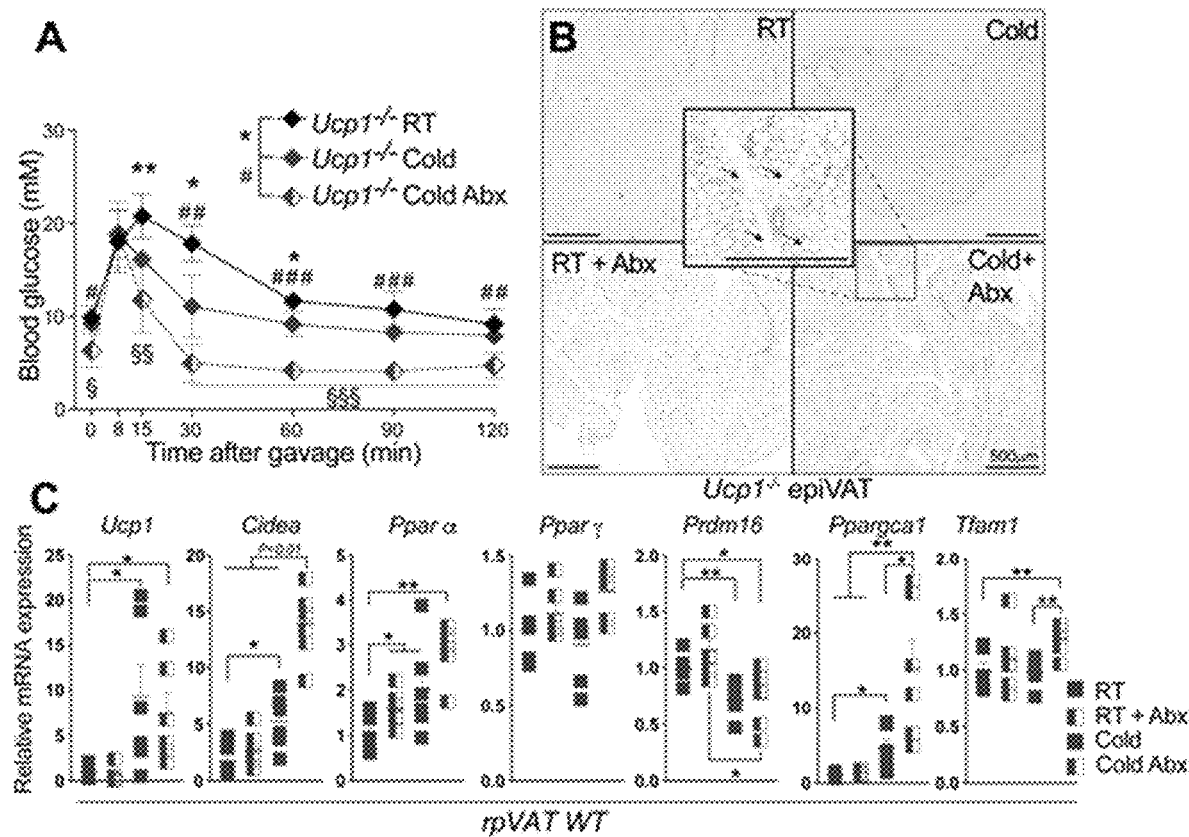
FIGS. 8A-C

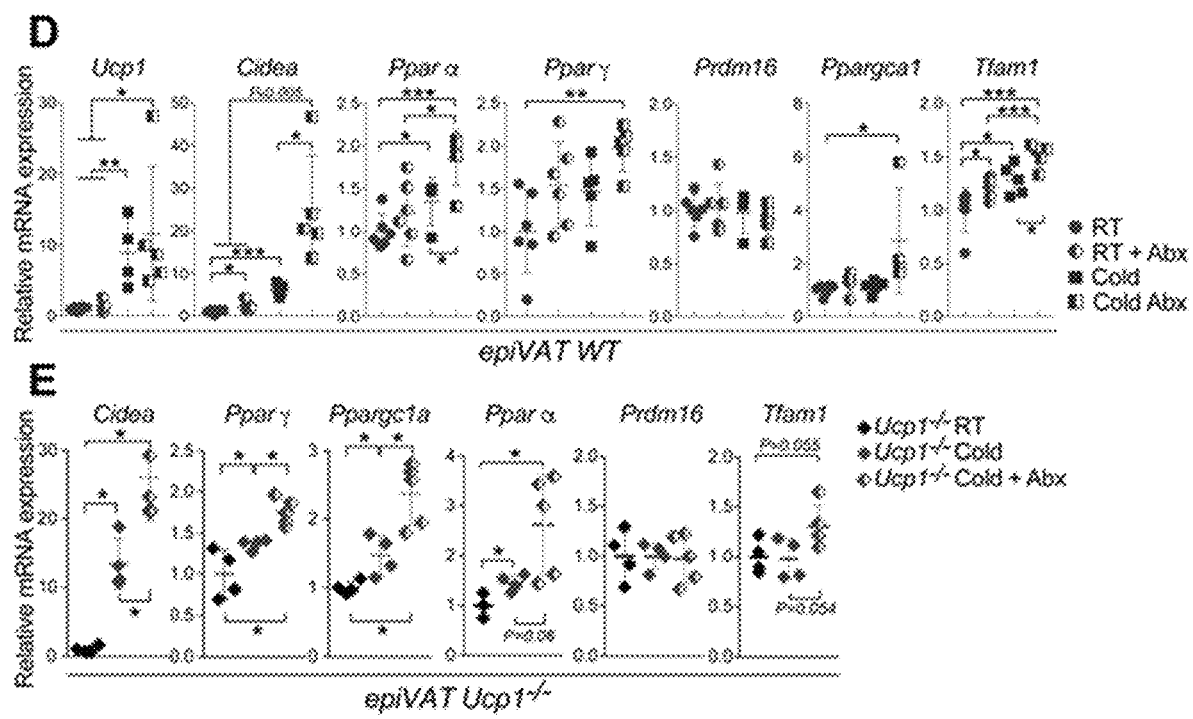
FIGS. 8D-E

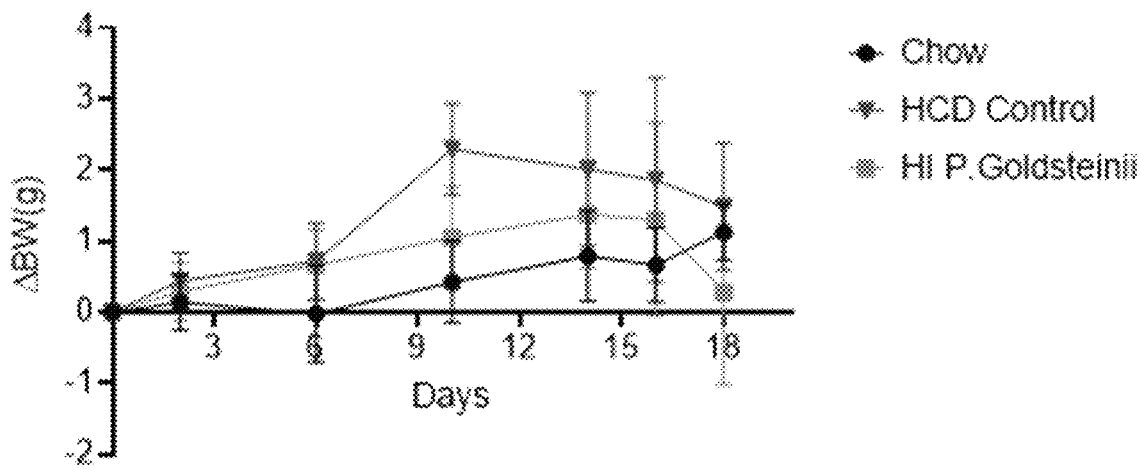
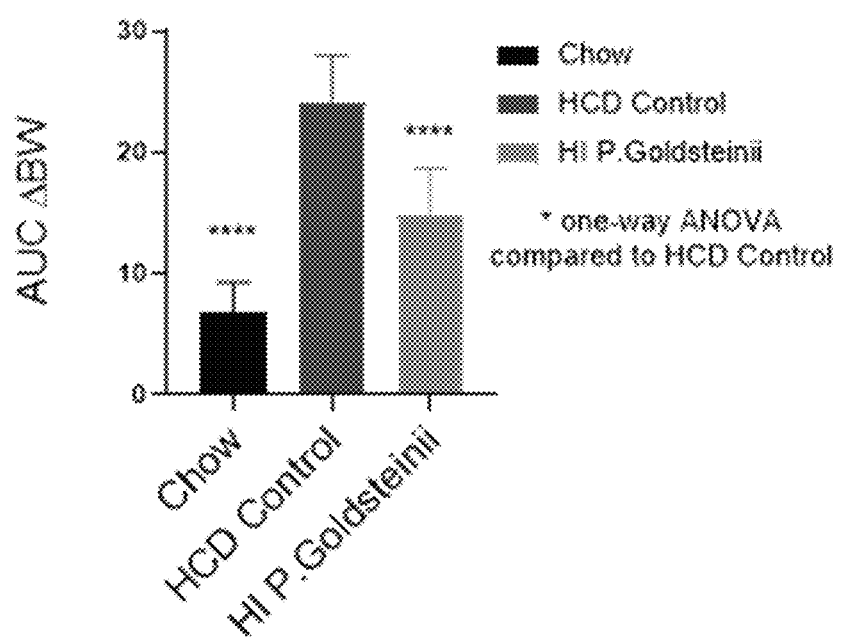
FIG. 10

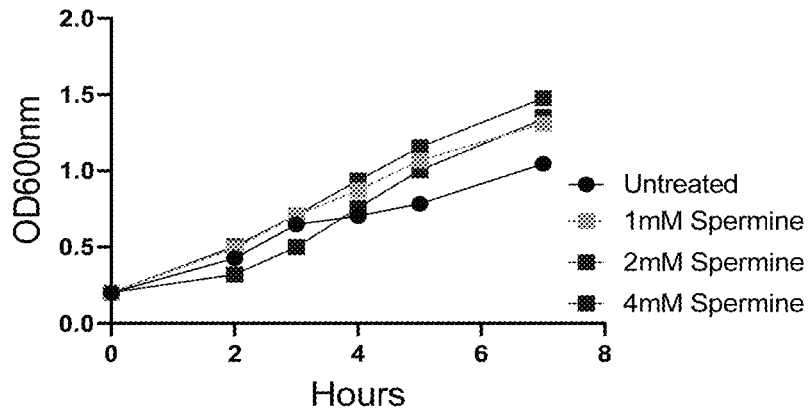
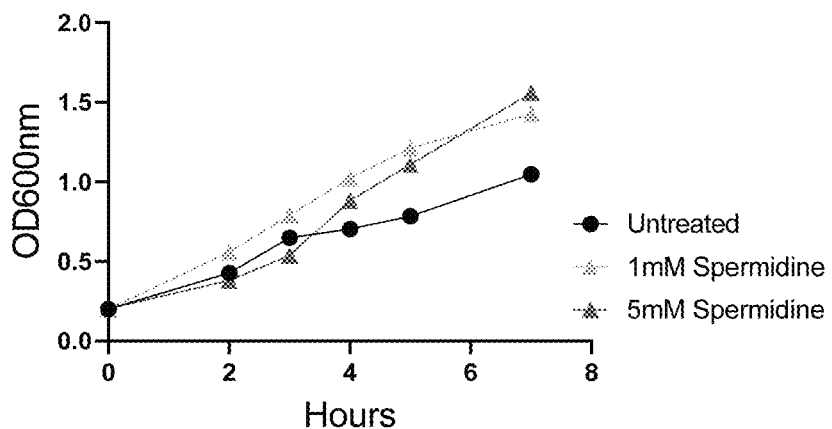
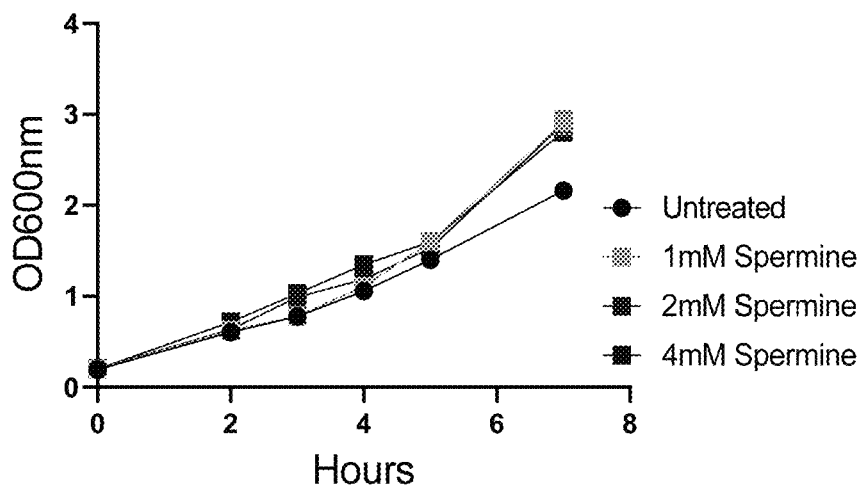
FIG. 12

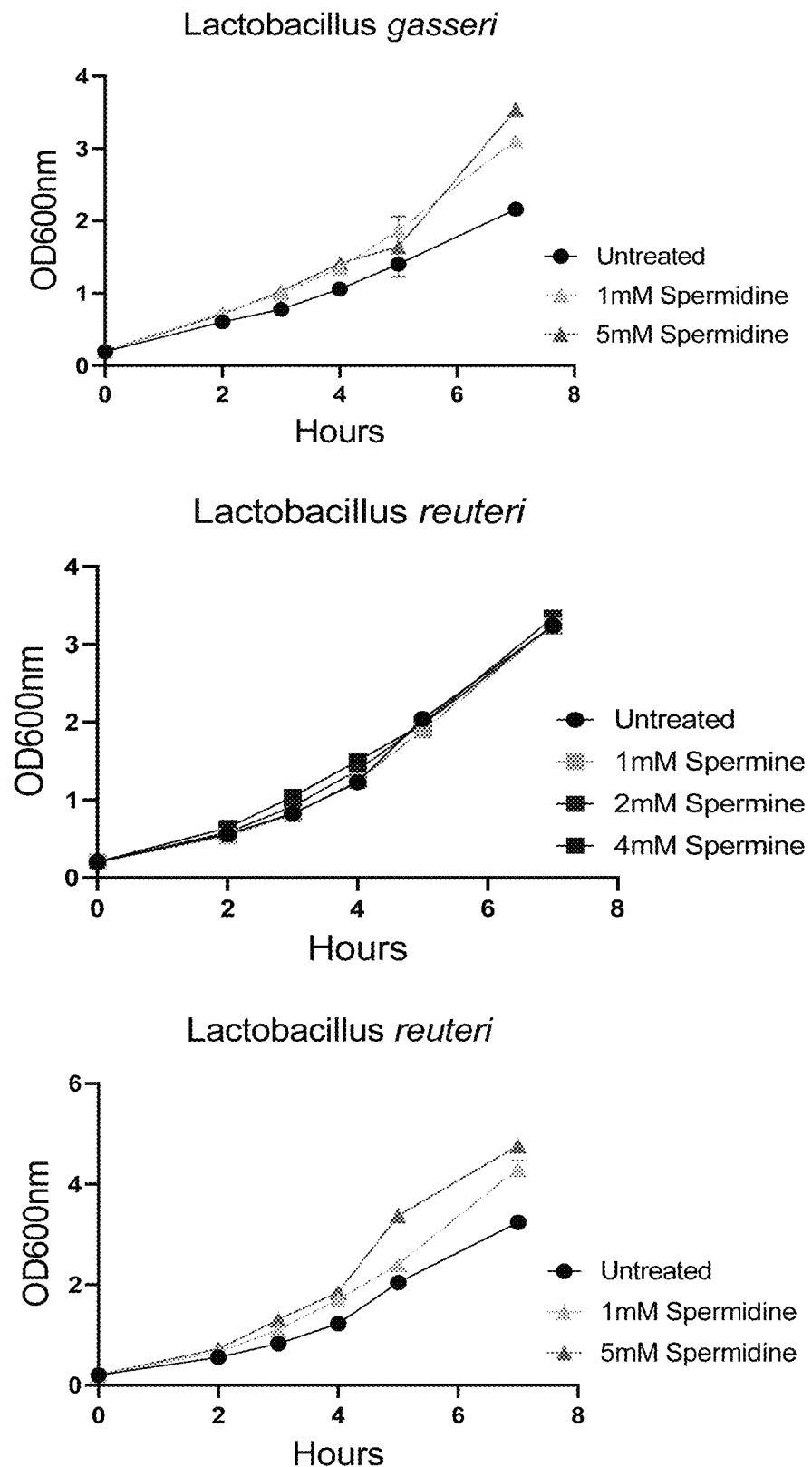
FIG. 12 (cot'd)

METHODS AND PROBIOTIC COMPOSITIONS FOR THE TREATMENT OF METABOLIC DISEASES AND DISORDERS

PRIORITY INFORMATION

This application claims the benefit of U.S. Provisional Patent Application No. 62/902,076, filed Sep. 18, 2019, and U.S. Provisional Patent Application No. 63/069,458, filed Aug. 24, 2020, the entirety of which are incorporated herein by reference.

BACKGROUND

1. Field of the Invention

The present invention relates generally to the fields of biology and medicine. More particularly, it concerns methods and compositions for the treatment of disease, such as metabolic diseases and disorders.

2. Description of Related Art

Obesity and type 2 diabetes remain serious clinical challenges. Obesity is a relatively common medical condition that can result in very serious adverse health consequences, such as heart disease, diabetes, high blood pressure, and certain cancers. Type 2 diabetes is characterized by resistance to insulin, and the disease can lead to several very serious health consequences including, e.g., neuropathies, skin problems, and/or kidney damage. Post-menopausal weight gain can also contribute to health problems in many individuals. The rates of obesity and type 2 diabetes are relatively high. For example, the number of people with obesity or type 2 diabetes in the U.S. alone are currently over 70 million people and over 30 million people, respectively.

The gut of a healthy mammalian subject is inhabited with microbiota that can affect human health. In some cases, the gut microbiome may play a role in the development of obesity, but the mechanism by which this may happen is complicated and not well understood (e.g., see Davis et al., 2016). For example, *Lactobacillus reuteri* has been observed to be increased in individuals with obesity (Million et al., 2012). Clearly there is a need for new methods for the treatment of obesity and type 2 diabetes.

SUMMARY OF THE INVENTION

The present disclosure is based, in part, on the discovery that specific bacteria (such as *Lactobacillus gasseri* or *Lactobacillus reuteri*) and/or heat-inactivated *Parabacteroides goldsteinii* can be used to treat obesity, reduce fatty liver, and improve insulin sensitivity. In some embodiments, pharmaceutical compositions or probiotic compositions that contain inactivated or heat-inactivated *Parabacteroides goldsteinii* are provided and may be administered to a mammalian subject used to treat obesity or a metabolic disease such as, e.g., type 2 diabetes or fatty liver disease. In some aspects, it has been observed that growing or expanding microbiota in polyamines, such as spermine or spermidine, can be used to treat a disease, such as a metabolic disease or disorder.

For example, as shown in the below examples and in contrast to the idea that typically only living microbiota bacteria such as *Parabacteroides goldsteinii* can affect the health of a mammalian subject, *Parabacteroides goldsteinii* were killed with heat (heat-inactivation) and the resulting composition was administered orally to ovariectomized mice, which resulted in improved glucose tolerance and metabolism, improved insulin sensitivity, and reduced fatty liver in vivo. Warm exposed animals also showed improved glucose tolerance following oral glucose load and increased insulin secretion. These results demonstrate that heat-inactivated *Parabacteroides goldsteinii* can be used to treat obesity or metabolic diseases, such as type 2 diabetes or fatty liver disease, in a mammalian subject in vivo. Enteric administration of *Lactobacillus gasseri* or *Lactobacillus reuteri* also improved glucose tolerance in vivo. Some of the beneficial effects of heat-inactivated *Parabacteroides goldsteinii* on blood glucose levels, oral glucose tolerance, and insulin sensitivity were observed to be more pronounced than those produced by *Akkermansia muciniphila*.

An aspect of the present invention relates to a method for treating a metabolic disease or disorder in a mammalian subject, comprising administering a composition to the gastrointestinal system of the subject, wherein the composition comprises inactivated *Parabacteroides goldsteinii*, the growth medium of *Parabacteroides goldsteinii*, or vesicles from *Parabacteroides goldsteinii*. In some embodiments, the inactivated *Parabacteroides goldsteinii* is heat-inactivated. In some embodiments, the inactivated *Parabacteroides goldsteinii* has been inactivated via exposure to a peroxide (e.g., hydrogen peroxide or hydrogen peroxide vapor). In some embodiments, the inactivated *Parabacteroides goldsteinii* has been inactivated via exposure to radiation or ionizing radiation (e.g., comprising or consisting of light having a wavelength of from about 400 to about 420 nm, more preferably about 400-410 nm, or about 405 nm). In some embodiments, the inactivated *Parabacteroides goldsteinii* has been inactivated via exposure to air plasma, ultrasound under pressure, exposure to an alcohol (e.g., ethanol, isopropanol, etc., for example at a concentration of about 40-100%, more preferably about 60-99%, 70-85% or 65%, 70%, 75% in solution, or any range therein), high hydrostatic pressure (HHP), or pulsed electric field (PEF). The composition may comprise extracellular vesicles from *Parabacteroides goldsteinii*. The composition may comprise from about $1\times10^8$ to about $1\times10^{13}$ cfu of the inactivated *Parabacteroides goldsteinii*. In some embodiments, the composition further comprises *Lactobacillus gasseri*, *Lactobacillus reuteri*, and/or *Akkermansia muciniphila*. In some embodiments, the composition is further defined as a pharmaceutical composition. In some embodiments, the composition is further defined as a probiotic composition. In some embodiments, the composition further comprises *Lactobacillus gasseri* or *Lactobacillus reuteri*. In some embodiments, the composition further comprises extracellular vesicles from *Lactobacillus gasseri* or *Lactobacillus reuteri*. In some embodiments, the pharmaceutical or probiotic composition is administered orally, colonically, via enema, via an orogastric tube, or via a nasogastric tube. In some embodiments, the inactivated *Parabacteroides goldsteinii* or vesicles from *Parabacteroides goldsteinii* is comprised in a pharmaceutical or probiotic composition that is resistant to degradation in the stomach but releases bacteria in the small intestine and/or large intestine of the subject. The pharmaceutical or probiotic composition may comprise an enteric coating, chitosan-alginate beads, or a hydrogel. In some embodiments, the enteric coating is a fatty acid, a wax, a shellac, a plastic such as a phthalate, CAP, CAT, PVAP, HPMCP, or a plant fiber. In some embodiments, the pharmaceutical or probiotic composition does not comprise an enteric coating. In some embodiments, the pharmaceutical or probiotic composition is a tablet or capsule. In some embodiments, the subject is a human (e.g., a postmenopausal woman). In some embodiments, the metabolic disease or disorder is obesity, type 2 diabetes, fatty liver disease (e.g., nonalcoholic fatty liver disease (NAFLD)), insulin resistance, or dyslipidemia. In some embodiments, microbiota in the composition has been purified or cultured. In some embodiments, the inactivated *Parabacteroides goldsteinii* have been inactivated by heating the bacteria, e.g., to about 95-105° C. for about 10-20 min, or to about 100° C. for about 15 min.

The method may further comprise enterically administering spermine and/or spermidine to the subject. In some embodiments, the method comprises enterically administering both spermine and spermidine to the subject. The method may comprise administering about 1-50 mg per kg body weight per day spermine to the subject, or any range derivable therein (e.g., 1-25, 2.5-15, 5-10, 5-25 mg spermine per kg body weight per day, etc.). In some embodiments, the method comprises administering about 1-50 mg per kg body weight per day spermidine to the subject, or any range derivable therein (e.g., 1-25, 2.5-15, 5-10, 5-25 mg spermidine per kg body weight per day, etc.). The composition may comprise the spermine and/or spermidine. In some embodiments, the composition comprises both spermine and spermidine. In some embodiments, the inactivated *Parabacteroides goldsteinii* are cultured or expanded in a medium comprising spermidine or spermine; for example, the *Parabacteroides goldsteinii* can be cultured or expanded in a medium comprising spermidine and/or spermine prior to inactivation via a method described herein or above (e.g., heat inactivation, exposure to a peroxide, etc.). In some embodiments, the medium comprises about 0.1-6 mM spermidine and/or about 0.1-6 mM spermine. In some embodiments, the subject is administered antibiotics and exposed to an environment of about 25-50° C., more preferably about 32-35° C. for at least about 15 minutes.

Another aspect of the present invention relates to a pharmaceutical or probiotic composition comprising heat-inactivated *Parabacteroides goldsteinii*, the growth medium of *Parabacteroides goldsteinii*, or vesicles from *Parabacteroides goldsteinii*; wherein the composition is formulated for delivery to the gastrointestinal system. In some embodiments, the composition comprises heat-inactivated *Parabacteroides goldsteinii*. The composition may further comprise *Lactobacillus gasseri* or *Lactobacillus reuteri*. The composition may further comprise extracellular vesicles from *Lactobacillus gasseri* or extracellular vesicles from *Lactobacillus reuteri*. In some embodiments, the pharmaceutical or probiotic composition is formulated for oral, colonic, enema, orogastric, or nasogastric administration. In some embodiments, the pharmaceutical or probiotic composition is resistant to degradation in the stomach but releases bacteria in the small intestine and/or large intestine of the subject. The pharmaceutical or probiotic composition may comprise an enteric coating, chitosan-alginate beads, or a hydrogel. In some embodiments, the enteric coating is a fatty acid, a wax, a shellac, a plastic such as a phthalate, CAP, CAT, PVAP, HPMCP, or a plant fiber. In some embodiments, the pharmaceutical or probiotic composition does not comprise an enteric coating. In some embodiments, the pharmaceutical or probiotic composition is a tablet or capsule. The pharmaceutical or probiotic composition may further comprise spermine and/or spermidine. The pharmaceutical or probiotic composition may comprise about 1-50 mg per kg body weight per day of spermine, or any range derivable therein (e.g., 1-25, 2.5-15, 5-10, 5-25 mg spermine per kg body weight per day, etc.). The pharmaceutical or probiotic composition may comprise about 1-50 mg per kg body weight per day of spermidine, or any range derivable therein (e.g., 1-25, 2.5-15, 5-10, 5-25 mg spermine per kg body weight per day, etc.). These amounts may be tailored for a human, e.g., weighing about 45-136 kg. In some embodiments, the pharmaceutical or probiotic composition further comprises both spermine and spermidine. In some embodiments, the *Parabacteroides goldsteinii* has been inactivated via exposure to a peroxide, ionizing radiation, heat, air plasma, ultrasound under pressure, an alcohol, high hydrostatic pressure (HHP), or pulsed electric field (PEF). In some embodiments, the *Parabacteroides goldsteinii* has been inactivated via exposure to a peroxide, ionizing radiation, or heat. The composition may be for use in treating a metabolic disease or disorder in a mammalian subject. The metabolic disease or disorder may be obesity, type 2 diabetes, fatty liver disease (e.g., nonalcoholic fatty liver disease (NAFLD)), insulin resistance, or dyslipidemia. In some embodiments, the subject is a human (e.g., a postmenopausal woman).

Another aspect of the present invention relates to a method of treating a metabolic disease or disorder in a mammalian subject comprising administering heat to the torso of the subject. The method may comprise placing the subject in a climate chamber with an ambient temperature of from about 65° C. to about 95° C. for about 3-30 minutes, about 3-15 minutes, about 3-10 minutes, or about 3-5 minutes. In some embodiments, the subject is repeatedly exposed to the climate chamber, with periods of time between each exposure. In some embodiments, a heating pad or heating lamp is applied to the torso, stomach, abdomen, head, legs, and/or feet of the subject, wherein the heating pad is from about 27° C. to about 50° C. or wherein the heating lamp is from about 60° C. to about 95° C. The heat may be applied for a period of from about 30 minutes to about 9 hours. In some embodiments, the heat is applied at least 1, 2, 3, 4, 5, 6, or 7 days a week for 1, 2, 3, 4, 5, 6, 7, 8, 9, or more weeks. In some embodiments, heat is repeatedly to the torso of the subject. In some embodiments, the metabolic disease or disorder is obesity, type 2 diabetes, fatty liver disease (e.g., nonalcoholic fatty liver disease (NAFLD)), insulin resistance, or dyslipidemia. The subject may be a human (e.g., a postmenopausal woman).

Yet another aspect of the present invention relates to a method of treating a metabolic disease or disorder in a mammalian subject comprising enterically administrating to the subject (i) vesicles from *Lactobacillus gasseri* or *Lactobacillus reuteri*, or (ii) a growth conditioned media from *Lactobacillus gasseri* or *Lactobacillus reuteri*. The method may further comprise administering from about $1 \times 10^8$ to about $1 \times 10^{13}$ cfu of a *Lactobacillus gasseri* or a *Lactobacillus reuteri* to the subject. The method may further comprise enterically administering spermidine and/or spermine to the subject. Nonetheless, in some embodiments the vesicles or growth conditioned media are enterically administered to the subject without administrating *Lactobacillus gasseri* or *Lactobacillus reuteri* to the subject. The subject may a human, such as for example a postmenopausal woman. The disease may be obesity, type 2 diabetes, fatty liver disease, insulin resistance, or dyslipidemia.

Yet another aspect of the present disclosure relates to a method of treating a disease or disorder in a mammalian subject, comprising: (i) expanding microbiota in a culture medium comprising spermidine or spermine, and (ii) enterically administering the microbiota to the subject. In some embodiments, the spermine or spermidine is present in the medium at a concentration of about 0.1-10 mM. The spermine may be present in the medium at a concentration of about 1-6, 1, 2, 3, 4, 5, 6 mM, or any range derivable therein (e.g., 1-3 mM, 2-3 mM, etc.). The spermidine may be present in the medium at a concentration of about 1-6, 1, 2, 3, 4, 5, 6 mM, or any range derivable therein. In some embodiments, the culture medium comprises both spermine and spermidine. The microbiota may comprise or consist of *Parabacteroides goldsteinii, Lactobacillus Reuteri*, and/or *Lactobacillus Gaseri*. The microbiota may comprise or consist of *Parabacteroides goldsteinii*. In some embodiments, the *Parabacteroides goldsteinii* are inactivated prior to administration to the subject. The *Parabacteroides goldsteinii* may be inactivated via exposure to a peroxide, ionizing radiation, heat, air plasma, ultrasound under pressure, an alcohol, high hydrostatic pressure (HHP), or pulsed electric field (PEF). In some embodiments, the *Parabacteroides goldsteinii* are inactivated via exposure to a peroxide, ionizing radiation, or heat. The peroxide may be hydrogen peroxide. In some embodiments, the *Parabacteroides goldsteinii* are inactivated by heating to about 95-105° C. for about 10-20 min. In some embodiments, the mammalian subject is a human. In some embodiments, the disease is a metabolic disease or disorder (e.g., obesity, type 2 diabetes, fatty liver disease, insulin resistance, or dyslipidemia). In some embodiments, the disease is a bone disease or the method comprises improving bone strength. The bone disease may be osteoporosis, osteomalacia, osteolysis, osteochondrodysplasias, periodontitis, rheumatoid arthritis, metabolic bone disease, a parathyroid disorder, steroid-induced osteoporosis, chemotherapy-induced bone loss, pre-menopausal bone loss, fragility and recurrent fractures, renal osteodystrophy, or Paget's disease.

*Lactobacillus gasseri* is a species of bacteria that has been identified as part of the vaginal flora and has been found in the lower digestive systems of women. Particular strains of *Lactobacillus gasseri* that may be used to treat a metabolic disease or disorder in a mammalian subject can include DSM 20077, DSM 107525, DSM 20243, DSM 20604, ATCC® 3332, ATCC® 2960, ATCC® BAA-2841, ATCC® PTA4483, ATCC® PTA4481, ATCC® PTA4484, ATCC® PTA4480, and/or ATCC® PTA4479. A variety of amounts of *Lactobacillus gasseri* may be administered to a mammalian subject (e.g., a human) to treat a metabolic disease or disorder as described herein (e.g., obesity, type 2 diabetes, fatty liver, etc.). For example, in some embodiments from about $1\times10^8$ to about $1\times10^{13}$ cfu of *Lactobacillus gasseri* can be administered to a mammalian subject, such as a human, to treat the metabolic disease or disorder.

*Lactobacillus reuteri* is a species of bacteria that has been found in the intestinal tract of healthy mammals. Particular strains of *Lactobacillus reuteri* that may be used to treat a metabolic disease or disorder in a mammalian subject include DSM 100191, DSM 100192, DSM 17509, DSM 20015, DSM 20016, DSM 20053, DSM 20056, DSM 28673, DSM 32035, ATCC® BAA-2837™, ATCC®55148, ATCC®53608, ATCC® 23272, ATCC® 23272D5, and/or ATCC® PTA6475. A variety of amounts of *Lactobacillus reuteri* may be administered to a mammalian subject (e.g., a human) to treat a metabolic disease or disorder as described herein (e.g., obesity, type 2 diabetes, fatty liver, etc.). For example, in some embodiments from about $1\times10^8$ to about $1\times10^{13}$ cfu of *Lactobacillus reuteri* can be administered to a mammalian subject, such as a human, to treat the metabolic disease or disorder.

*Parabacteroides goldsteinii* is a gram-negative, obligately anaerobic non-spore-forming and non-motile bacterium that has been isolated from human blood. Particular strains of *Parabacteroides goldsteinii* that may be used to treat a metabolic disease or disorder in a mammalian subject include DSM 19448 and/or DSM 29187. A variety of amounts of *Parabacteroides goldsteinii* may be administered to a mammalian subject (e.g., a human) to treat a metabolic disease or disorder as described herein (e.g., obesity, type 2 diabetes, fatty liver, etc.). For example, in some embodiments from about $1\times10^8$ to about $1\times10^{13}$ cfu of inactivated *Parabacteroides goldsteinii* can be administered to a mammalian subject, such as a human, to treat the metabolic disease or disorder. As shown in the below examples, heat-inactivated *Parabacteroides goldsteinii* can be administered to treat a metabolic disease or disorder. Methods of heat inactivation that may be used to prepare heat-inactivated *Parabacteroides goldsteinii* are well known and include heating up the bacteria to about 100° C. for about 15 minutes (Wu et al., 2019). *Parabacteroides goldsteinii* might also be conserved by freezing or by dehydration. A variety of methods can be used to generate inactivated *Parabacteroides goldsteinii*. For example, in some embodiments, the bacteria may be irradiated or killed by radiation, exposure to ethanol, or autoclaving (e.g., as described in Lin et al., 2015.). In some embodiments, the *Parabacteroides goldsteinii* can be inactivated by exposure to light comprising or consisting of light having a wavelength of about 405 nm (e.g., Maclean et al., 2009). The inactivated *Parabacteroides goldsteinii* can be generated via exposure to air plasma, such as a direct-current, cold-atmospheric-pressure air plasma microjet (e.g., Tian et al., 2010). The inactivated *Parabacteroides goldsteinii* can be generated via exposure to hydrogen peroxide or hydrogen peroxide vapor (e.g., Malik et al., 2013; Erttmann et al., 2019; Grigoryan et al., UDC 579.67). The inactivated *Parabacteroides goldsteinii* can be generated via exposure to ionizing irradiation, ultrasound under pressure, high hydrostatic pressure (HHP), and/or pulsed electric field (PEF) (e.g., Manas, et al., 2005). In some preferred embodiments, *Parabacteroides goldsteinii* are killed using heat inactivation.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

Other objects feature and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Oral glucose tolerance test (OGTT) in 8 weeks old male mice exposed 1 month at 34° C. (FIG. 1B) Associated insulin release at time point 0, 7 and 15 min.

(FIG. 2A) Oral glucose tolerance test in 16 weeks old ovariectomized, or sham operated female mice. (FIG. 2B) Oral glucose tolerance test in ovariectomized mice kept at RT or at 34° C. for 2 months.

(FIG. 3A) Blood glucose levels in mice supplemented with heat inactivated *Parabacteroides goldsteinii* (OVA Gold) after 12 or 6 h of. (FIG. 3B) Oral glucose tolerance test (left), and area under the curve (right) in ovariectomized mice kept at RT supplemented with heat inactivated *Parabacteroides goldsteinii*, or live *Akkermansia muciniphila*. (FIG. 3C) Insulin tolerance test measured after an injection of 0.5 U/kg of insulin followed by monitoring of glycemia over 2 h in mice as in FIGS. 3A-B).

(FIG. 6A) Oral glucose tolerance test after 3 weeks of treatment. Inserts on the left show area under the curve (AU, upper) and fasting starting glycemia (lower). (FIG. 6B) Weight of adipose tissues at sacrifice of C57bl/6J mice after 4 weeks of treatment (epiVAT, or rpVAT: epididymal or retroperitoneal visceral adipose tissue; ingSAT: inguinal subcutaneous adipose tissue; rpVAT: retroperitoneal visceral adipose tissue; iBAT: interscapular brown adipose tissue). [3H]-2DG glucose analog deposition in adipose tissue after and intraperitoneal injection. Bars show mean±s.d. (n=6-8 per group). Statistics was done using unpaired two-tailed Student's t-test.*P≤0.05, P≤0.01, *P≤0.001.

FIGS. 7A-B: (FIG. 7A) Representative H&E staining of visceral adipose tissue of C57Bl/6 mice after 30 days of treatment as indicated. Black arrows indicate multilocular adipocytes. (FIG. 7B) Oxygen consumption rates measured using Seahorse analyzer at basal conditions after 30 days of treatment. Significance was calculated using unpaired two-tailed Student's t-test. ***P≤0.001.

FIGS. 8A-E: (FIG. 8A) Oral glucose tolerance test in Ucp1-KO mice after 3 weeks of treatment. (FIG. 8B) Representative H&E staining of visceral adipose tissue of Ucp1-KO mice after 30 days of treatment as indicated. Black arrows indicate multilocular adipocytes. (FIGS. 8C-E) Relative gene expression of the thermogenic genes in rpVAT, and epiVAT of WT (FIG. 8C and FIG. 8D), or Ucp1-KO (FIG. 8E) mice, normalized to Tbp. Significance in A, C and D was calculated using unpaired two-tailed Student's t-test. ***P≤0.001.

FIG. 10: Body weight of mice fed high caloric diet, following oral supplementation of HI Parabacteroides Goldsteinii. Data show body weight change following the start of the bacterial gavage (left), or area under curve from the panel in left (right) Significance is calculated based on One-Way ANOVA; ****P<0.0001.

FIG. 12: Supplementation of spermine or spermidine promotes growth of beneficial bacteria in vitro.

DESCRIPTION OF ILLUSTRATIVE EMBODIMENTS

I. Definitions

Figure 1A:
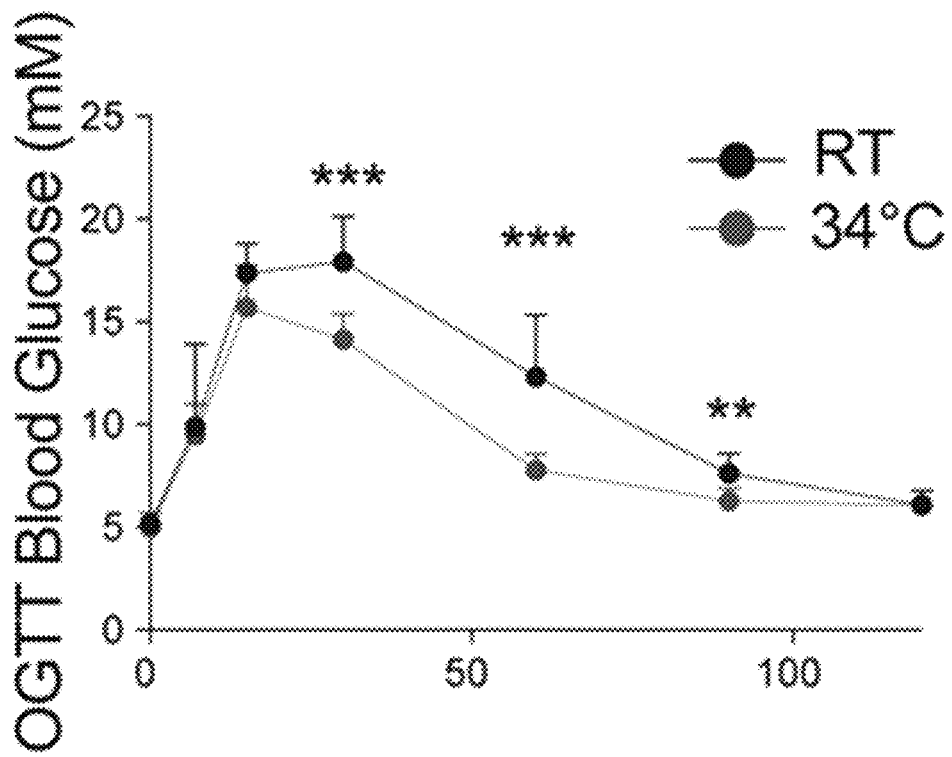
FIGS. 1A-B: Warm exposure improves tolerance to orally administered glucose.

A "bacterial composition" is a composition that comprises one of more types of bacteria (e.g., live, dried, or heat-inactivated) or extracellular vesicles (i.e., secreted extracellular vesicles) from bacteria. In some embodiments, the bacteria are from the Clostridiaceae, Lactobacillaceae, and/or Porphyromonadaceae families. Specific bacteria that are contemplated include *Lactobacillus gasseri*, *Lactobacillus reuteri*, and *Parabacteroides goldsteinii* (e.g., live or heat-inactivated *P. goldsteinii*). In some preferred embodiments, an inactivated *Parabacteroides goldsteinii* is used that has been inactivated using heat, freezing, or drying.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a bacterial composition means that amount of the bacterial composition which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

As used herein, the term "patient" or "subject" refers to a living mammalian organism, such as a human, monkey, cow, sheep, goat, dog, cat, mouse, rat, guinea pig, or transgenic non-human species thereof. In certain embodiments, the patient or subject is a primate. Non-limiting examples of human patients are adults, juveniles, and infants.

A "pharmaceutically acceptable carrier," "drug carrier," or simply "carrier" is a pharmaceutically acceptable substance formulated along with the active ingredient that is involved in carrying, delivering and/or transporting a biological agent. Carriers may be used to improve the delivery and the effectiveness of the active ingredient, including for example, controlled-release technology to modulate drug bioavailability, decrease drug metabolism, and/or reduce drug toxicity. Some carriers may increase the effectiveness of delivery of the active ingredient to the specific target sites. Examples of carriers include: liposomes, microspheres (e.g., made of or comprising poly(lactic-co-glycolic) acid), albumin microspheres, synthetic polymers, nanofibers, protein-DNA complexes, protein conjugates, erythrocytes, virosomes, hydrogels, starches, and dendrimers. In some embodiments, the carrier comprises an enteric coating (e.g., a fatty acid, a wax, a shellac, a plastic such as a phthalate, CAP, CAT, PVAP, HPMCP, or a plant fiber) to reduce or slow degradation in the stomach, chitosan-alginate beads, or a hydrogel.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

II. Warm Microbiota

As shown in the below examples, a variety of bacteria have been observed in warm microbiota, or the microbiota obtained from mammalian subjects living in warmer environments. Warm microbiota include Clostridialeace-assimilate spp., *Lactobacillus* spp. (e.g., *Lactobacillus gasseri* or *Lactobacillus reuteri*), *Bifidobacteriaceae* spp. (e.g., *Bifidobacterium longum*), *Parabacteroides* spp. (e.g., *Parabacteroides goldsteinii*) and *Akkermansia* spp. (e.g., *Akkermansia muciniphila*). In some embodiments, it is anticipated that bacteria described in any one of Tables 1-5 may be included in a pharmaceutical composition or probiotic composition disclosed herein. In some embodiments, the pharmaceutical composition or probiotic composition may contain *Lactobacillus reuteri, Lactobacillus acidophilus*, and/or *Lactobacillus rhamnosus*. As shown in the examples, therapeutic responses can also be observed when using heat-inactivated *Parabacteroides goldsteinii*.

In various embodiments, it is anticipated that 1, 2, 3, 4, 5, 6, or more of the following types of bacteria may be included in a pharmaceutical composition or probiotic composition disclosed herein. For example, the 1, 2, 3, 4, 5, 6, or more of Clostridialeace-assimilate spp., *Lactobacillus* spp. (e.g., *Lactobacillus reuteri, Lactobacillus gasseri, Lactobacillus acidophilus*, and/or *Lactobacillus rhamnosus*), *Bifidobacteriaceae* spp. (e.g., *Bifidobacterium longum*), Parabacteroides spp. (e.g., *Parabacteroides goldsteinii*) and *Akkermansia* spp. (e.g., *Akkermansia muciniphila*) may be included in a pharmaceutical or probiotic composition disclosed herein and/or administered to a mammalian subject, such as a human patient, to treat a metabolic disease or disorder. Various interactions between gut microbiota and physiology may be used in combination with the present disclosure (e.g., as described in Ohlsson and Sjogren, 2015). *Lactobacillus* species such as *Lactobacillus reuteri* (Britton et al., 2014; also recently described in humans in Nilsson et al., 2018), *Lactobacillus acidophilus* (Dar et al., 2018), and/or *Lactobacillus rhamnosus* (Li et al., 2016) may be included in compositions for the treatment of a metabolic disease or disorder. In other embodiments, heat (e.g., from a heating chamber, heating pad, or a heating lamp) may be applied to the subject (e.g., to the whole body, or a specific zone, such as the torso, stomach, limbs, and/or abdomen) to treat a metabolic disease or disorder described herein, such as for example obesity, type 2 diabetes, or fatty liver. In some embodiments, the heat applied may promote growth of warm microbiota.

III. Inactivated *Parabacteroides goldsteinii*

Inactivated *Parabacteroides goldsteinii* can be produced via a variety of methods. In some embodiments, the inactivated *Parabacteroides goldsteinii* is inactivated via exposure to heat. Nonetheless, it is anticipated that other methods of inactivation can be used to generate inactivated *Parabacteroides goldsteinii* that may exert similar effect(s) and can be used for the treatment of a metabolic disease or disorder as described herein (e.g., obesity, diabetes, etc.). For example, the inactivated *P. goldsteinii* can be generated via exposure of the bacteria to light (e.g., radiation or ionizing radiation), air plasma, pressure (e.g., ultrasound under pressure, high hydrostatic pressure), a peroxide (e.g., hydrogen peroxide), an alcohol (e.g., ethanol), exposure to cold temperatures or freezing, dehydration, lyophilization, or pulsed electric field (PEF); in some embodiments, one or more of the foregoing methods for inactivation of bacteria can be used in combination with application of heat in order to produce inactivated *P. goldsteinii* that can be used, e.g., for the treatment of a metabolic disease or disorder as described herein. In some embodiments, a composition as described herein may include both live and inactivated *Parabacteroides goldsteinii*.

A variety of methods can be used to generate heat-inactivated *Parabacteroides goldsteinii*. For example, the bacteria may be heated to at least 95° C., at least 100° C., or about 100° C. for at least 10 minutes, 10-20 minutes, or about 15 minutes, e.g., as described in Wu et al. (2019). It is anticipated that autoclaving or heating in a solution (e.g., boiling in water) can also be used. Generally, heat may inactivate the bacteria via one or more of membrane damage, loss of nutrients and ions, ribosome aggregation, DNA strand breaks, inactivation of essential enzymes, and protein coagulation. Additional methods of inactivation that may be used with the present invention are described, e.g., in Lin et al. (2015). After generating the inactivated (e.g., heat-inactivated) *P. goldsteinii*, the bacteria can be subsequently dried, frozen, or lyophilized, if desired. In some preferred embodiments, *Parabacteroides goldsteinii* are killed using heat inactivation.

Inactivated *P. goldsteinii* can also be generated based on exposure to radiation, such as ionizing radiation. In some embodiments, the bacteria can be inactivated by exposure to light comprising or consisting of light having a wavelength of about 405 nm. For example, a light-emitting diode (LED) array producing light with a wavelength of about 405 can be used to inactivate bacteria (e.g., Maclean et al., 2009). In some embodiments, the radiation may be ultraviolet (UV) radiation having a wavelength of from about 240 nm to about 280 nm. In some embodiments, the radiation is ionizing radiation, such as x-rays.

The inactivated *Parabacteroides goldsteinii* can be generated via exposure to a peroxide, such as for example hydrogen peroxide. The hydrogen peroxide may be contacted with the bacteria in a solution. In some embodiments, the bacteria are contacted with a hydrogen peroxide vapor in order to inactivate the bacteria. For example, the bacteria may be exposed to hydrogen peroxide vapor of about 10-100 mg/m$^3$ (ppm) for about 1.5-48 hours (e.g., Malik et al., 2013). Hydrogen peroxide can be applied either as a liquid or as a vapor for inactivating bacteria. In some instances, the mode of action of hydrogen peroxide in vapor form may result in increased intensive oxidation of a range of biological macromolecules than do aqueous solutions of hydrogen peroxide (Finnegan et al., 2010). Similar to heat-inactivation, using hydrogen peroxide for inactivation of bacteria has the advantage that it decomposes into non-toxic byproducts after reacting with a bacteria. In some embodiments, it is anticipated that a solution of 1-2% hydrogen peroxide can be contacted with *P. goldsteinii* for about 5-10 minutes in order to inactivate the bacteria. In some embodiments, a combination of heat and hydrogen peroxide can be used to inactivate *P. goldsteinii*.

A variety of other methods for inactivating *P. goldsteinii* can also be used. For example, the bacteria may be inactivated by contacting the bacteria with an alcohol (e.g., ethanol, methanol, propanol, or isopropanol) at a particular concentration (e.g., at least 70% v/v alcohol, such as 70% ethyl alcohol) in order to inactivate the bacteria.

The inactivated *Parabacteroides goldsteinii* may also be generated via exposure to air plasma, such as a direct-current, cold-atmospheric-pressure air plasma microjet (e.g., Tian et al., 2010); for example, after about 10 min of plasma treatment, a decrease in the pH may be observed due to the reaction of NO$_x$ produced in the air plasma with water at the gas-liquid interface.

The inactivated *Parabacteroides goldsteinii* can be generated via exposure to ionizing irradiation (e.g., gamma rays produced from cobalt-60, electron beams, or X-rays). Generally, the dosage of the ionizing radiation applied to the bacteria is preferably sufficient to damage DNA of the bacteria and/or prevent further growth of the bacteria.

Ultrasound under pressure or high hydrostatic pressure (HHP) can also be used to inactivate bacteria. In some embodiments, pressures of from about 100 to 1000 MPa are applied in order to inactivate bacteria. The effectiveness of HHP has been demonstrated in the field of food sanitization. Ultrasound is defined as sound waves with frequencies above the threshold for human hearing (>16 kHz). In some embodiments, ultrasound application can be used in combination with an external hydrostatic pressure (e.g., up to 600 kPa of manosonication (MS)]) and/or application of heat in order to inactivate the *P. goldsteinii*.

Pulsed electric field (PEF) can also be (e.g., Manas et al., 2005). PEF approaches generally involve the application of short duration (e.g., 1-100 μs) high electric field pulses (10-50 kV cm$^{-1}$) to sample between two electrodes. In various embodiments, it is anticipated that a combination of one or more of the foregoing methods may be used to produce the inactivated *P. goldsteinii*.

IV. Spermine and Spermidine

In some aspects, spermine and/or spermidine may be enterically administered to a mammalian subject, such as a human, to treat a metabolic disease or disorder as described herein (e.g., diabetes, obesity, etc.) or a bone disease or disorder. For example the bone disease or disorder may be, e.g., osteoporosis, osteomalacia, osteolysis, osteochondrodysplasias, periodontitis, rheumatoid arthritis, metabolic bone disease, a parathyroid disorder, steroid-induced osteoporosis, chemotherapy-induced bone loss, pre-menopausal bone loss, fragility and recurrent fractures, renal osteodystrophy, or Paget's disease. In some embodiments, the spermidine and/or spermine may be administered in combination with an inactivated *P. goldsteinii* as described herein (e.g., a heat-inactivated *P. goldsteinii*). In some embodiments, the spermine or spermidine may be administered in combination with another live or inactivated microbiota as described herein (e.g., *L. Reuteri*, *L. Gasseri*, and/or *A. Muciniphila*), optionally in combination with live or inactivated *P. goldsteinii*. As shown in the below examples, enteric administration of microbiota cultured in spermidine or spermine reduced obesity in an animal model in vivo, and reductions in the total fat (including a decrease in subcutaneous, visceral, and brown adipose tissues) were observed.

Spermidine (N-(3-(aminopropyl)-1,4-butane diamine) and spermine (N, N'-bis (3-aminopropyl)-1,4-butane diamine) are naturally occurring polyamines, and can function as regulators for a variety of cellular processes including DNA stability, transcription, translation, apoptosis, and may affect cellular growth and differentiation (Igarashi et al., 2010). In some studies, spermine and spermidine inhibited experimental inflammation in association with suppressed expression of pro-inflammatory cytokines (Soda et al., 2005). Spermine and spermidine may affect osteoclast differentiation (Yamamoto et al., 2012), and a correlation between polyamine levels and symptoms of skeletal muscle hypertrophy (Turchanowa et al., 2000), Alzheimer's disease (Morrison et al., 1995), and ischaemia (Paschen et al., 1987) have been observed.

A variety of dosages of spermine and/or spermidine may be enterically administered to the subject, preferably a human to treat a metabolic disease or disorder as described herein. Spermine and/or spermidine can be administered in concentrations of from about 0.3 mM to about 3 mM each, or more preferably about 0.3-1 mM, or about 0.5 mM (e.g., orally administered, for example in drinking water), and these concentrations were shown to be effective in mouse models of osteoporosis and aging. In experimental studies 0.5 mM in drinking water, which is the equivalent of 18.2 mg/kg body weight, also showed beneficial effects of polyamine supplementation on ovariectomy induced bone loss and lifespan extension. In some embodiments, a range between 1-50, 2-40, 5-25, or 15-20 mg/kg body weight per day, or any range derivable therein, may be used to treat a metabolic disease or disorder as described herein.

In some aspects, microbiota is cultured in spermine and/or spermidine prior to administration to a mammalian subject, such as a human, to treat a metabolic disease or disorder, or a bone disease or disorder, as described herein. For example, in some embodiments, microbiota are cultured in 0.1-10 mM, 1-7 mM, or more preferably 1-5 mM, or 0.5, 1, 2, 3, 4, or 5 mM, or any range derivable therein, of spermine and/or spermidine, prior to administration to the subject to treat the metabolic disease or disorder. The microbiota may comprise or consist of *Parabacteroides goldsteinii, Lactobacillus Reuteri* and/or *Lactobacillus Gaseri*. In some embodiments, the *Parabacteroides goldsteinii* that has been cultured or expanded in spermine and/or spermidine is subsequently inactivated via a method as described herein (e.g., heat inactivation, exposure to hydrogen peroxide, etc.), and the inactivated *P. goldsteinii* can be included in a pharmaceutical or probiotic composition or enterically administered to a human to treat a metabolic disease or disorder as described herein. In some embodiments, the microbiota includes living and/or inactivated *Akkermansia muciniphila* in combination with *Parabacteroides goldsteinii* (living and/or inactivated), Lactobacillus *Reuteri* and/or *Lactobacillus Gaseri*; and in some embodiments, the microbiota includes both living and inactivated *Akkermansia mucuniphila*.

V. Pharmaceutical Formulations and Routes of Administration

In another aspect, for administration to a patient in need of such treatment, pharmaceutical formulations (also referred to as bacterial formulations or pharmaceutical compositions) comprise a therapeutically effective amount of a live or heat-inactivated bacterial composition disclosed herein formulated with one or more excipients and/or carriers appropriate to the indicated route of administration. In some embodiments, the bacteria disclosed herein are formulated in a manner amenable for the treatment of human and/or veterinary patients. In some embodiments, formulation comprises admixing or combining one or more of the bacteria disclosed herein (e.g., warm microbiota, and/or heat-inactivated *Parabacteroides goldsteinii*) with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the bacteria may be slurried in water, polyethylene glycol, propylene glycol, ethanol, corn oil, cottonseed oil, peanut oil, sesame oil, benzyl alcohol, sodium chloride, and/or various buffers. In some embodiments, the pharmaceutical formulations may be subjected to pharmaceutical operations, such as sterilization, and/or may contain carriers and/or excipients such as preservatives, stabilizers, wetting agents, emulsifiers, encapsulating agents such as lipids, dendrimers, polymers, proteins such as albumin, nucleic acids, and buffers.

In some embodiments, the pharmaceutical formulation comprises inactivated (e.g., heat-inactivated) *Parabacteroides goldsteinii*. A variety of amounts of heat-inactivated *Parabacteroides goldsteinii* may be included, for example from about $1 \times 10^8$ to about $1 \times 10^{13}$ cfu. In some embodiments, the heat-inactivated *Parabacteroides goldsteinii* is included in a pharmaceutical composition or a probiotic composition formulated for oral or enteric administration. For single, or mixed (cultivated) bacteria administration, the heat-inactivated *Parabacteroides goldsteinii* can be administered orally (e.g., in form of tablets). For the fecal microbiota transplantation from donors (FMT), heat-inactivated *Parabacteroides goldsteinii* can for example be added to the microbiota that is delivered to the gastrointestinal system, e.g., via nasogastric tube or intracolonically.

Bacterial formulations may be administered by a variety of methods, e.g., orally, intracolonically, intranasally, intrarectally, via a catheter, via a lavage, via a nasogastric tube, via local delivery, or via a method for fecal microbiota transplantation (FMT). Depending on the route of administration, the bacterial compositions disclosed herein may be coated in a material to protect the bacterial compositions from the action of acids and other natural conditions which may inactivate the bacterial compositions. To administer the bacterial composition, it may be necessary to coat the bacterial composition with, or co-administer the bacterial composition with, a material to prevent its inactivation. In some embodiments, the bacterial composition may be administered to a patient in an appropriate carrier, for example, polymers, hydrogels, liposomes, starches, or a diluent. Pharmaceutically acceptable diluents include saline and aqueous buffer solutions. Liposomes include water-in-oil-in-water CGF emulsions as well as conventional liposomes.

Formulations may be employed to protect the bacterial compositions from the harsh gastric environment (Govander et al., 2014). Gastro-resistant polymers and coatings have been shown to supply protection against the harsh gastric environment. These coatings included enteric coated tablets and capsules that site-specifically deliver the administered probiotic bacteria to the intestinal system. These enteric coats are often pH selective and allow for protection against the harsh gastric conditions and subsequently dissolve in the alkali media of the intestinal system (Calinescu et al., 2005 and Yang et al., 2002). Non-limiting examples of excipients that may employed in the formulation of bacterial compositions are hydroxypropyl methylcellulose phthalate and carboxymethyl high amylose starch. Excipients may be combined to enhance delivery of the bacterial composition to the gastrointestinal tract. For example, carboxymethyl high amylose starch may be combined with chitosan for delivery of the bacterial composition to the colon. Formulations may include different polymers with different properties, or similar polymers with different properties, depending on the site of intended delivery to deliver the bacterial composition to different areas of the gastrointestinal tract (Yang et al., 2002).

The bacterial compositions disclosed herein may also be administered orally, intracolonically, intranasally, intrarectally, via a catheter, via a lavage, via a nasogastric tube, via local delivery, or via a method for fecal microbiota transplantation (FMT). The bacterial composition may be in the form of a dispersion. Dispersions can be prepared in glycerol, liquid polyethylene glycols, and mixtures thereof and in oils.

In some embodiments, the carrier comprises an enteric coating to reduce or slow degradation in the stomach. For example, the enteric coating may be a fatty acid, a wax, a shellac, a plastic such as a phthalate, CAP, CAT, PVAP, HPMCP, or a plant fiber (e.g., Hussan et al., 2012). In some embodiments, the pharmaceutical or probiotic composition may contain chitosan-alginate beads, or a hydrogel. Nonetheless, it is anticipated that in some embodiments, The bacterial compositions disclosed herein can be administered orally, for example, with an inert diluent or an assimilable edible carrier. The bacterial compositions and other ingredients may also be enclosed in a hard or soft-shell gelatin capsule, compressed into tablets, or incorporated directly into the patient's diet. For oral therapeutic administration, the bacterial compositions disclosed herein may be incorporated with excipients and used in the form of ingestible tablets, buccal tablets, troches, capsules, elixirs, suspensions, syrups, wafers, and the like. The percentage of the therapeutic agent in the compositions and preparations may, of course, be varied. The amount of the therapeutic agent in such pharmaceutical formulations is such that a suitable dosage will be obtained.

In some embodiments, it may be advantageous to formulate compositions in dosage unit form for ease of administration and uniformity of dosage. Dosage unit form as used herein refers to physically discrete units suited as unitary dosages for the patients to be treated; each unit containing a predetermined quantity of therapeutic agent calculated to produce the desired therapeutic effect in association with the required pharmaceutical carrier. In some embodiments, the specification for the dosage unit forms of the invention are dictated by and directly dependent on (a) the unique characteristics of the therapeutic agent and the particular therapeutic effect to be achieved, and (b) the limitations inherent in the art of compounding such a therapeutic agent for the treatment of a selected condition in a patient. In some embodiments, the active agent(s) are administered at a therapeutically effective dosage sufficient to treat a condition associated with a condition in a patient. For example, the efficacy of a bacterial composition can be evaluated in an animal model system that may be predictive of efficacy in treating the disease in a human or another animal.

In some embodiments, the effective dose range for the therapeutic agent can be extrapolated from effective doses determined in animal studies for a variety of different animals. Precise amounts of the therapeutic composition depend on the judgment of the practitioner and are specific to each individual. Other factors affecting the dose include the physical and clinical state of the patient, the route of administration, the intended goal of treatment and the potency, stability, and toxicity of the particular therapeutic formulation.

The actual dosage amount of a bacterial composition of the present disclosure administered to a patient may be determined by physical and physiological factors such as type of animal treated, age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

Single or multiple doses of the agents are contemplated. Desired time intervals for delivery of multiple doses can be determined by one of ordinary skill in the art employing no more than routine experimentation. As an example, patients may be administered two doses daily at approximately 12-hour intervals. In some embodiments, the agent is administered once a day.

The composition comprising a bacterial composition (e.g., heat-inactivated *Parabacteroides goldsteinii*) may be administered on a routine schedule. As used herein, a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the patient has eaten or will eat.

VI. Extracellular Vesicles of Bacteria

In some embodiments, extracellular vesicles from bacteria described herein may be administered to a subject to treat a metabolic disease or disorder. For examples, extracellular vesicles (EVs) may be produced via methods as described, for example, in Chelakkot et al., 2018, or Choi et al., 2015. It is anticipated that EVs from *Parabacteroides goldsteinii*, *Lactobacillus gasseri*, or *Lactobacillus reuteri* may be used to treat a metabolic disease or disorder as described herein (e.g., obesity, type 2 diabetes, fatty liver).

Extracellular vesicles (EVs) are lipid bilayer structures secreted from the gut microbiota, including from both Gram-negative and -positive bacteria (Ellis and Kuehn, 2010 and Lee et al., 2009). A variety of bacteria constitutively produce EVs, defined as spherical lipid bilayers with an average diameter of 20-200 nm (Lee et al., 2007). EVs are composed of proteins, lipids, nucleic acids, lipopolysaccharides and other virulence factors associated with pathogenesis (Horstman and Kuehn, 2002, Hong et al., 2011, and Kim et al., 2013). EVs released by bacteria may have diverse roles in the microbial community, and some data suggests that they may transfer genetic material and proteins from the bacteria to the host (Kuehn and Nesty, 2005). EVs may directly interact with immune cells and epithelial cells to initiate several signaling pathways and may affect or mediate host-pathogen interactions.

For example, in some embodiments, EVs may be prepared via the following approach. Bacterial species or warm microbiota may be cultured under aerobic or anaerobic conditions (e.g., 95% $N_2$ 5% $CO_2$ at 37° C.) until desired (e.g., when the optical density at 600 nm reaches 1.5, as previously described; Derrien et al., 2004). Isolation of EVs may be performed as previously described in Kang et al., 2013. More specifically, bacterial cultures may be pelleted at 10 000 g for 20 min, and the supernatant may then be filtered through a 0.45-μm vacuum filter. The filtrate can be enriched, e.g., using QuixStand (GE Healthcare, Little Chalfont, UK) and subsequently filtered through a 0.22-µm bottle-top filter. The filtrate may then be pelleted by ultra-centrifugation (e.g., in a 45 Ti rotor at 150 000 g for 2 h at 4° C.). The final pellets may then be resuspended in phosphate-buffered saline (PBS) and stored at −80° C. EVs may be analyzed, if desired, by transmission electron microscopy, dynamic light scattering, and/or sodium dodecyl sulfate-polyacrylamide gel electrophoresis (SDS-PAGE) followed by gel staining with Coomassie Brilliant Blue R-250. The amount of protein or DNA extracted from the EVs can be measured and used to evaluate the quantity of EVs obtained.

VII. Metabolic Diseases and Disorders

It is anticipated that a variety of metabolic diseases or disorders may be treated with the methods and bacterial compositions described herein. For example, a bacterial composition as described herein (e.g., live bacteria, heat inactivated bacteria, lyophilized bacteria, bacteria in a pharmaceutical composition, or secreted extracellular vesicles of the bacteria) may be administered enterically or to the gastrointestinal tract of a subject to treat a metabolic disease or disorder. In some embodiments, the bacterial composition is heat-inactivated *Parabacteroides goldsteinii*. In some embodiments, the metabolic disease or disorder is obesity, fatty liver disease, type 2 diabetes, insulin intolerance, or dyslipidemia. Without wishing to be bound by any theory, the below examples provide date methods and bacterial compositions provided herein (e.g., heat-inactivated *Parabacteroides goldsteinii*) may be used to improve glucose tolerance and metabolism, improve insulin secretion, and reduce fatty liver.

The prevalence of obesity, measured by body mass index, has risen to unacceptable levels in both men and women in the United States and worldwide with resultant hazardous health implications. Genetic, environmental, and behavioral factors influence the development of obesity. In adults, classification systems (*World Health Organ Tech Rep Ser.*, 2000) and obesity guidelines (Jensen et al., 2014) define healthy body weight as a BMI between 18.5 and 24.9 kg/m$^2$, overweight between 25.0 and 29.9 kg/m$^2$, and obesity ≥30 kg/m$^2$. In children and adolescents, the U.S. Centers for Disease Control and Prevention (CDC) BMI-for-age growth charts define overweight as a BMI at or above the 90th percentile of standard weight and obesity as a BMI above the 95$^{th}$ percentile of standard weight. Obesity is associated with and contributes to a shortened life span, type 2 diabetes mellitus, cardiovascular disease, some cancers, kidney disease, obstructive sleep apnea, gout, osteoarthritis, and hepatobiliary disease, among others (Bray et al., 2018). Weight loss can reduce these diseases in a dose-related manner, with the more weight lost, the better the outcome.

Fatty Liver Disease, also known as hepatic steatosis, is a condition where excess fat builds up in the liver. The fatty liver disease can be non-alcoholic fatty liver disease (NAFLD) or alcoholic liver disease. Non-alcoholic fatty liver disease (NAFLD) is a common cause of chronic liver disease, and its worldwide prevalence continues to increase with the growing obesity epidemic. Non-alcoholic fatty liver disease is the most common cause of elevated liver enzymes. Within the NAFLD spectrum, typically only non-alcoholic steatohepatitis progresses to cirrhosis and hepatocellular carcinoma (Vernon et al., 2011). With the growing epidemic of obesity, the prevalence and impact of NAFLD continues to increase.

Type 2 diabetes (T2D), formerly known as adult-onset diabetes, is a form of diabetes that is characterized by high blood sugar, insulin resistance, and relative lack of insulin. Type 2 diabetes can be diagnosed using a glycated hemoglobin (A1C) test to determine average blood sugar levels, and diagnosis can also be performed using a random blood sugar test, a fasting blood sugar test, or an oral glucose tolerance test. Type 2 diabetes is the most common form of diabetes and can be caused by several factors, including obesity, physical inactivity, and genes. Insulin can help achieve ideal hemoglobin A1c goals for patients with type 2 diabetes (Wallia et al., 2014). Obesity in some cases can result in insulin resistance and is common in people with type 2 diabetes. In some embodiments, a bacterial composition as disclosed herein (e.g., heat-inactivated *Parabacteroides goldsteinii*) is administered to a mammalian subject, such as a human, in combination with another therapy for type 2 diabetes such as, e.g., metformin, a sulfonylurea, a meglitinide, a thiazolidinedione, a DPP-4 inhibitor, a GLP-1 receptor agonist (e.g., exenatide), a SGLT2 inhibitor, or insulin.

Dyslipidemia is characterized by abnormal levels of lipids in the blood, such as: elevation of plasma cholesterol, triglycerides (TGs), or both; increased low-density lipoprotein (LDL) or very-low-density lipoprotein (VLDL) levels; low high-density lipoprotein cholesterol (HDL) levels; or low HDL cholesterol level. In some embodiments, the dyslipidemia is a hyperlipidemia (increase in blood lipids). Dyslipidemia may contribute to the development of atherosclerosis.

VIII. Temperature and Gut Microbiology

As shown herein, exposure to warm environments can change the microbiota of a mammalian subject, and the resulting "warm microbiota" has been shown herein to produce effects including improvements in glucose tolerance and reduced fatty liver that may be particularly beneficial for treating a metabolic disease or disorder such as obesity, type 2 diabetes, or fatty liver. Some living organisms adapt to the perpetual change of their surrounding environment. One such external parameter is temperature, which can vary from below −35° C. to more than 40° C. and depends on seasonal periodicity and on the time of the day.

Homeotherm animals need to conserve a constant body temperature; as a result, they have developed different strategies to adapt to these external fluctuations. In rodents, a thermogenic program is engaged upon cold stimulation, including shivering thermogenesis from the muscles and non-shivering thermogenesis from the adipose tissue. During warm exposure, in contrast, the thermogenic program is blunted and the energy expenditure reduced accordingly (Kaiyala et al., 2012). Additionally, to dissipate the heat excess, rodents increase skin vasodilation at specific locations where the surface to body ratio is high in order to maximize the heat loss. This is the case in the ears and tail (Meyer et al., 2017). Interestingly, scarce reports have suggested that upon longer exposure to elevated temperature, rodents adapt to maximize their ability to dissipate heat through an increase in their tail and ear length/surface (Alhilli and Wright, 1983, Ashoub, 1958, and Harland, 1960).

The intestinal flora has been shown to affect some aspects of host physiology. Adaptation to cold exposure was shown to be partially mediated by the gut microbiota (Chevalier et al., 2015). The present disclosure shows that warm exposure can benefit metabolic characteristics (including improved insulin sensitivity, improved glucose tolerance, and reduced fatty liver), and gut flora alterations play a role in these changes. Thus, these beneficial effects may be utilized in the treatment of metabolic diseases and disorders.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 1B:
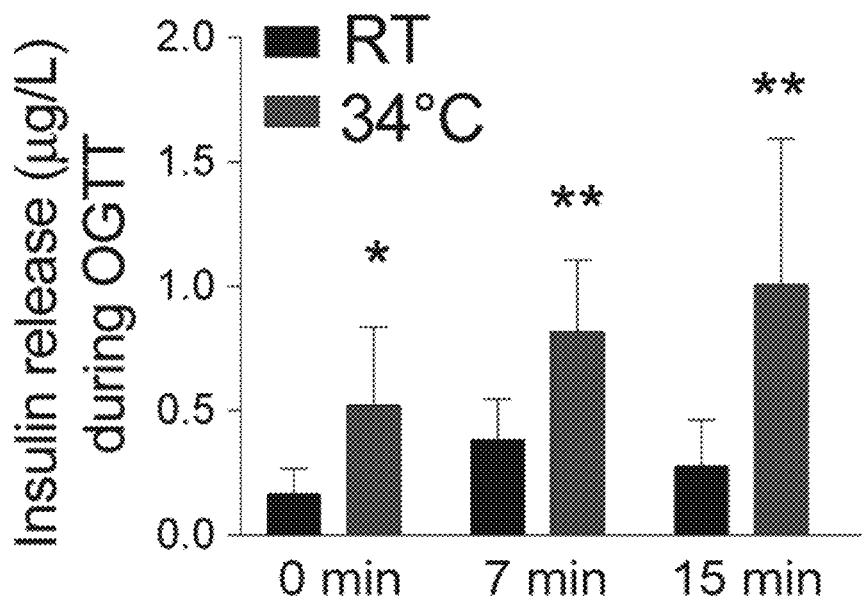
Figure 2A:
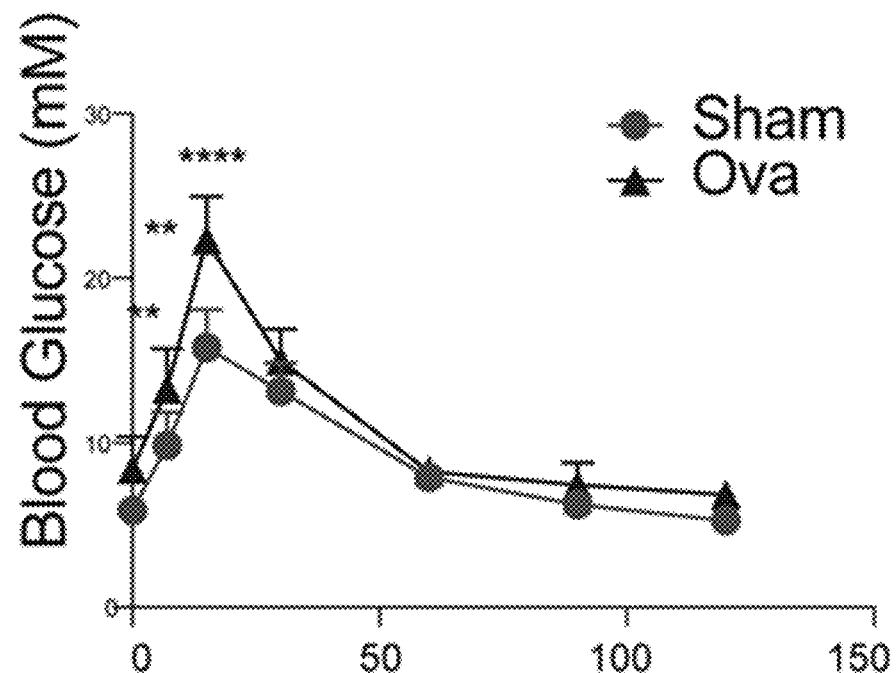
FIGS. 2A-B: Warm exposure prevents the ovariectomy-induced oral glucose intolerance.
Figure 2B:
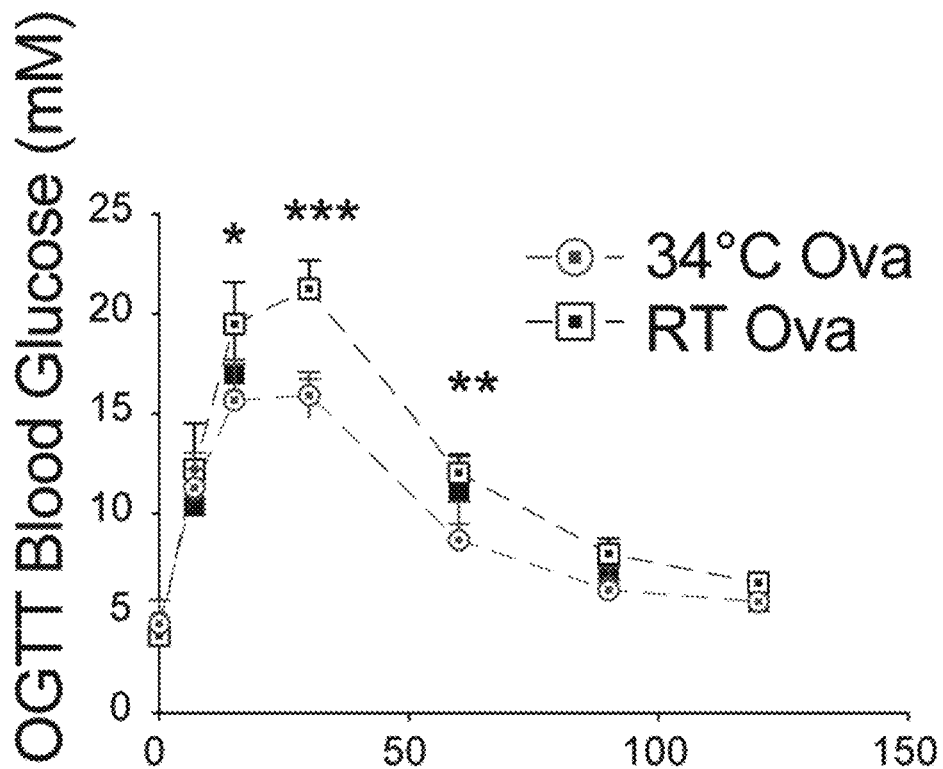

Warm Exposure, and Heat-Inactivated *Parabacteroides goldsteinii* Improve Glucose Metabolism and Reduce Fatty Liver in Post-Menopausal Mouse Model To assess the effect of warm temperature on the glucose metabolism 8-week-old male mice were cared for at 34° C. for one month. Monitoring their glucose tolerance, that warm exposed animals showed improved glucose tolerance following oral glucose load (FIG. 1A), which was associated with an increased insulin secretion (FIG. 1B). Whether similar effects would be observed in metabolically challenged condition, such as the post-menopausal weight gain and glucose intolerance was then investigated. Mimicking post-menopausal weight gain and glucose intolerance by ovariectomy, estrogen deficiency worsened the glucose tolerance as was observed during an oral glucose tolerance test (OGTT, FIG. 2A). Interestingly, the reduced glucose tolerance was rescued when the mice were exposed to warm temperature (FIG. 2B), indicating that warm exposure improves tolerance to glucose in a post-menopausal mouse model.

Since warm exposure can change the microbiota composition, the inventors investigated whether some of the bacteria that are most predominantly changed could mimic the warm exposure phenotype. One of the most consistently regulated bacteria were *Parabacteroides goldsteinii, Akkermansia muciniphila, Lactobacillus Reuteri* and *Lactobacillus Gasseri*, all being increased during warm exposure. To assess their individual effect on the observed phenotype, the bacteria were freshly grown and gavaged every second day to ovariectomized mice.

Figure 3A:
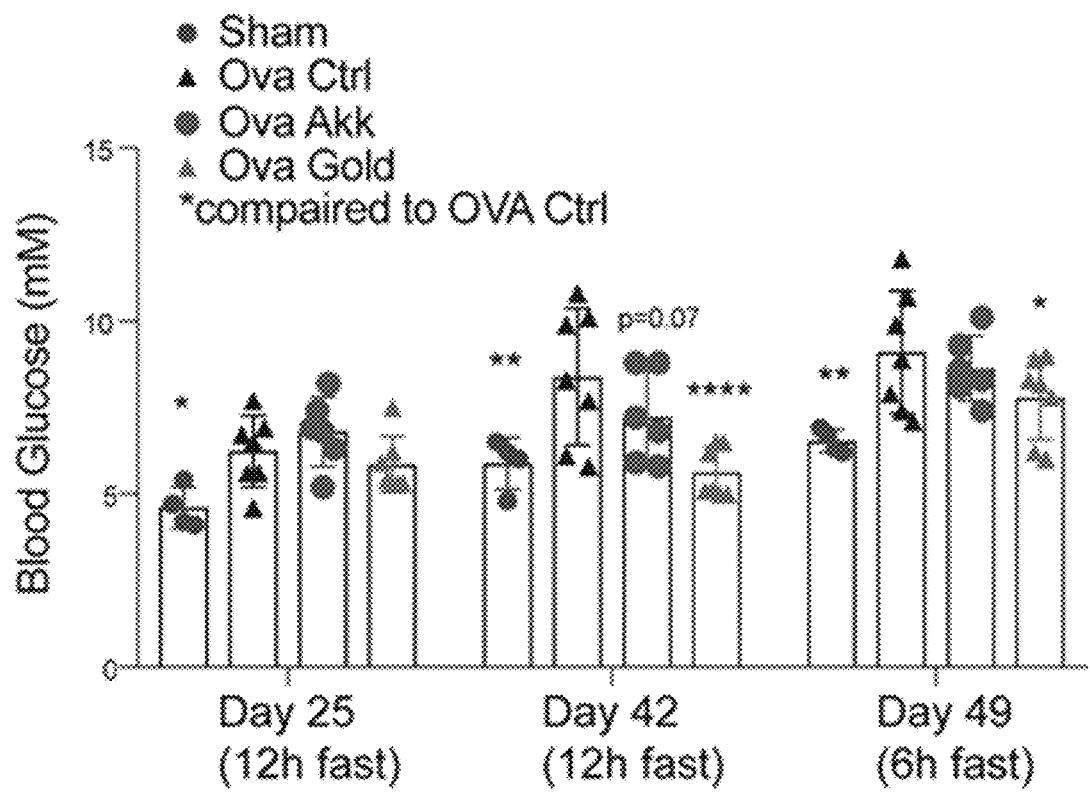
FIGS. 3A-C: Heat-inactivated *Parabacteroides goldsteinii* protects against ovariectomy-induced hyperglycemia and improves glucose tolerance and insulin sensitivity.
Figure 3B:
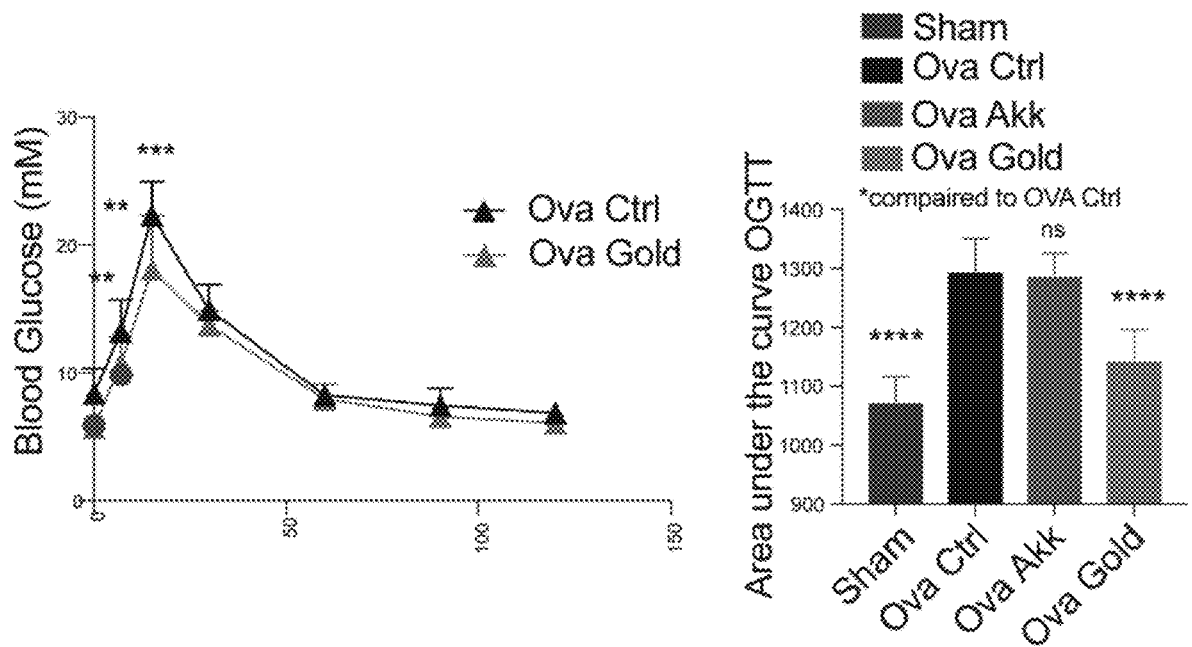
Figure 3C:
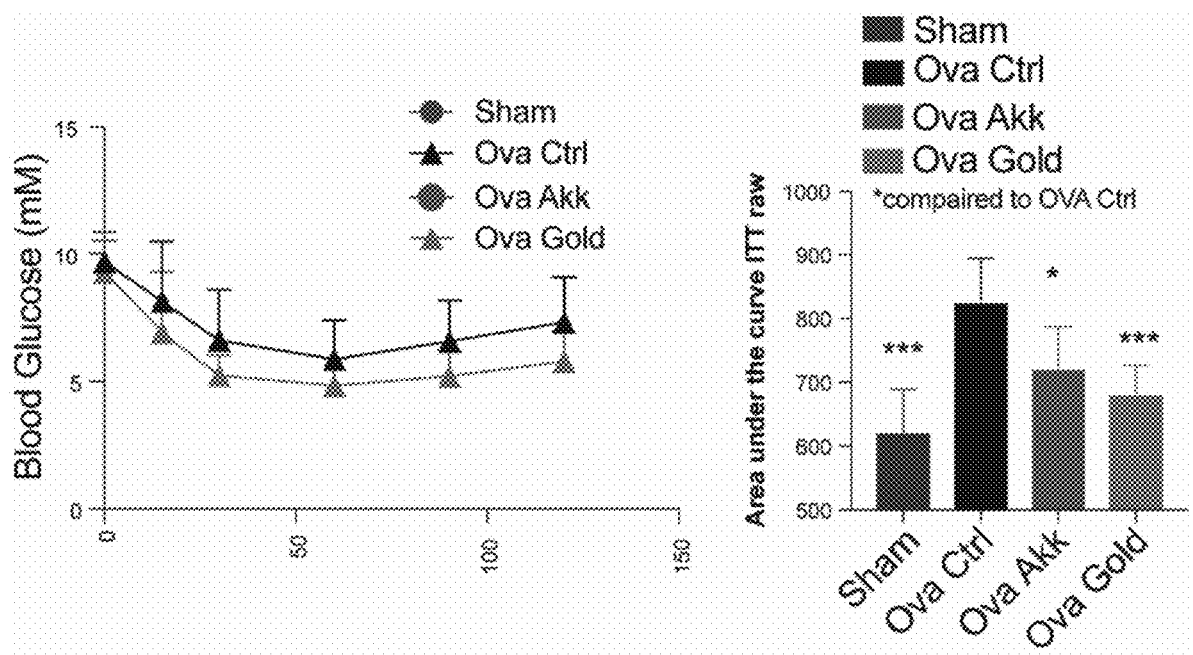
Figure 4:
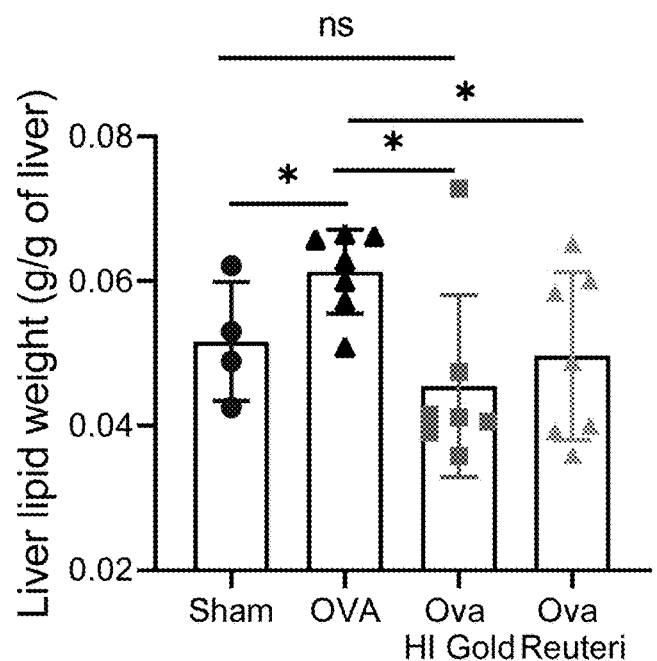
FIG. 4: Heat-inactivated *Parabacteroides goldsteinii* prevents ovariectomy-induced liver fat accumulation. Liver lipid content in ovariectomized mice kept at RT supplemented with heat inactivated *Parabacteroides goldsteinii*.

Additional testing was performed using heat-inactivated (HI) *Parabacteroides goldsteinii*. Supplementation of heat-inactivated *Parabacteroides goldsteinii* (OVA Gold) was able to prevent the ovariectomy-induced hyperglycemia, effect observed after either 12, or 6 h of fasting (FIG. 3A). Additionally, HI *Parabacteroides goldsteinii* supplementation improved the oral glucose tolerance (FIG. 3B) and in part the insulin sensitivity (FIG. 3C) in the ovariectomized mice. The effect of the HI *Parabacteroides goldsteinii* was observed to be more pronounced than those produced by *Akkermansia muciniphila*, a bacteria described to improve metabolic health during obesity. HI *P. Goldsteinii* was also observed to reduce the accumulation of lipids in the liver (FIG. 4). These data support the idea that HI *P. Goldsteinii* may be used to treat or prevent fatty liver disease.

Figure 5:
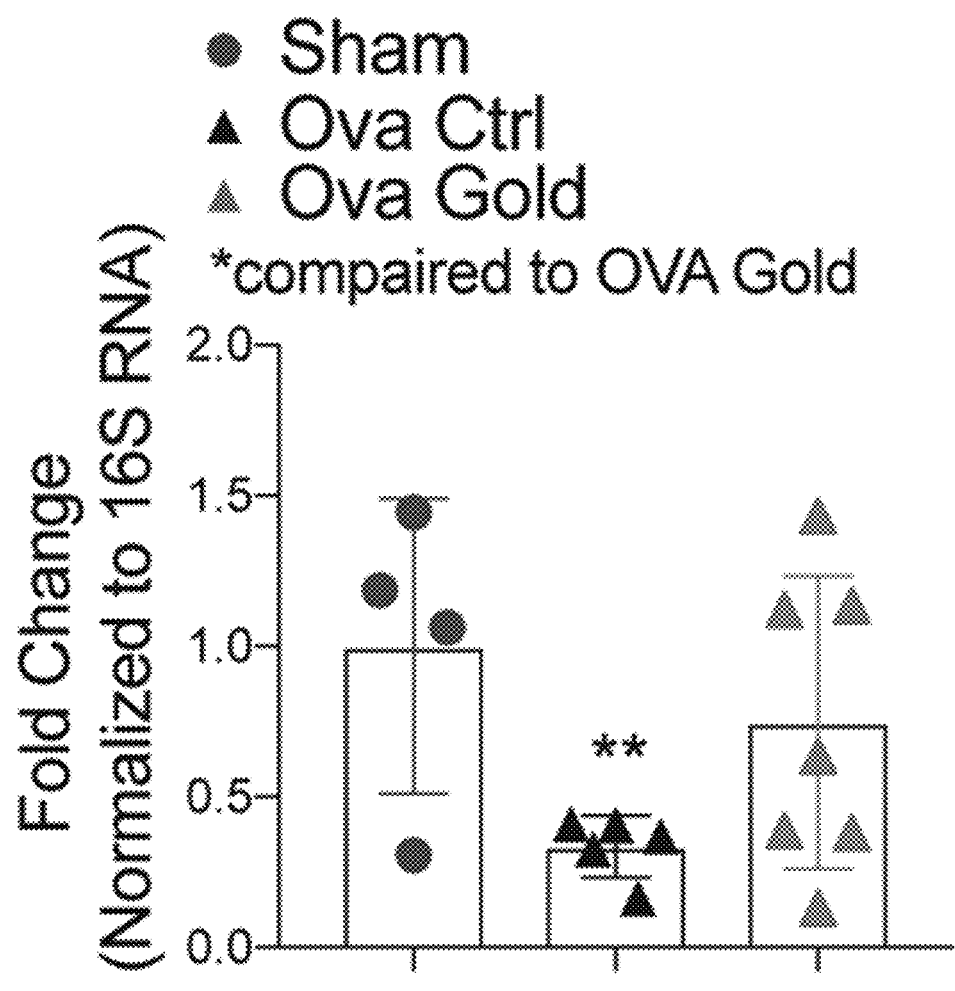
FIG. 5: Supplementation of the heat-inactivated *Parabacteroides goldsteinii* prevents the ovariectomy-induced endogenous *Parabacteroides goldsteinii* loss. Fecal *Parabacteroides goldsteinii* from ovariectomized mice kept at RT supplemented with heat inactivated *Parabacteroides goldsteinii*, 48 hrs after the last administration.

Supplementation of the heat-inactivated *Parabacteroides goldsteinii* also increased the levels of the detected *Parabacteroides goldsteinii* 48 hours after the last administration. As shown in FIG. 5, supplementation of the heat-inactivated *Parabacteroides goldsteinii* prevented ovariectomy-induced endogenous *Parabacteroides goldsteinii* loss. Without wishing to be bound by any theory, since typically the clearance of the supplemented heat-inactivated *Parabacteroides goldsteinii* should not take more than 24 hrs, one possibility is that this treatment might reduce ovariectomy-induced endogenous *Parabacteroides goldsteinii* loss or might promote its growth.

To further investigate the therapeutic potential of the heat inactivated *Parabacteroides goldsteinii* in improving the metabolic outcome, the effect of supplementation of heat-inactivated *Parabacteroides goldsteinii* in mouse models with diet-induced obesity can be tested. The secretory vesicles from *Parabacteroides goldsteinii* can also be obtained, and the vesicles can be used to test whether the vesicles can reproduce the effects of supplemented heat-inactivated *Parabacteroides goldsteinii*. Since *Lactobacillus Reuteri* and *Lactobacillus Gasseri* supplementation in the ovariectomized mice also improved glucose tolerance and insulin sensitivity, secretory vesicles of these bacteria can also be isolated and used to determine if they can exhibit similar therapeutic effects. Growth media from *Parabacteroides goldsteinii, Lactobacillus Reuteri*, and/or *Lactobacillus Gasseri* can be obtained and further tested, e.g., in mouse models with diet-induced obesity.

Example 2

Methods for Treatment of Obesity

Figure 6A:
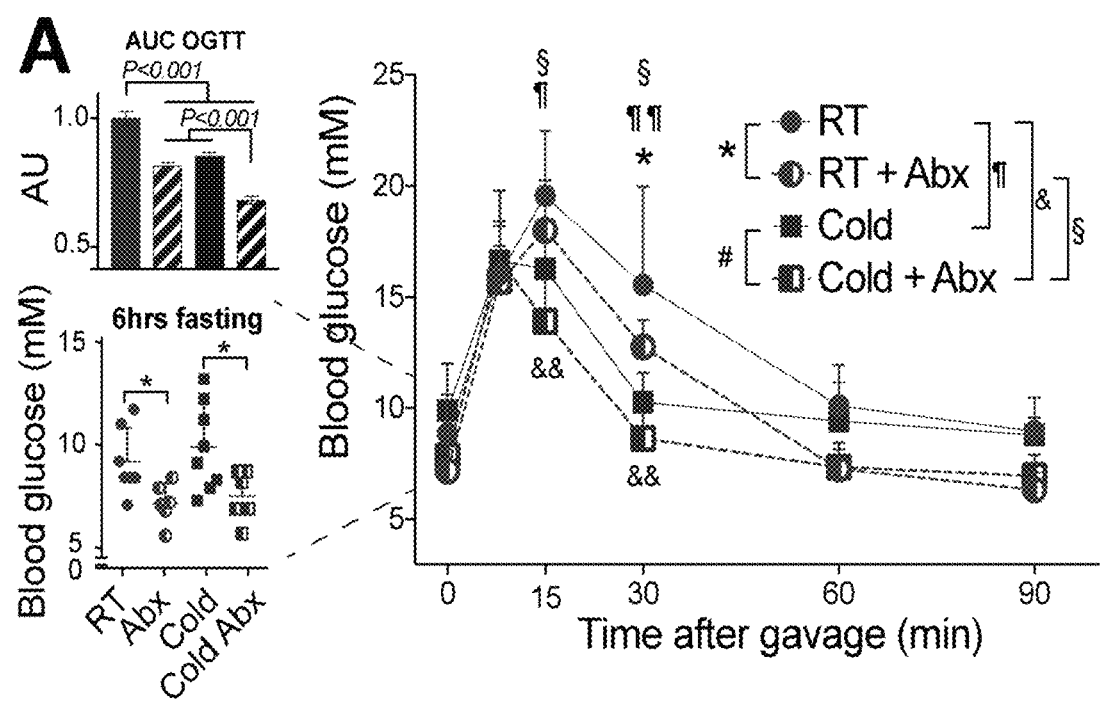
FIGS. 6A-C.
Figure 6B:
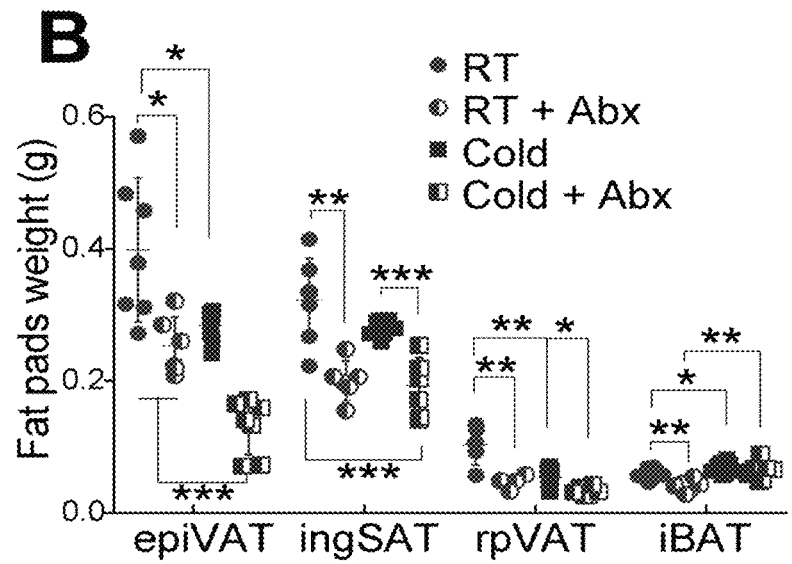
Figure 6C:
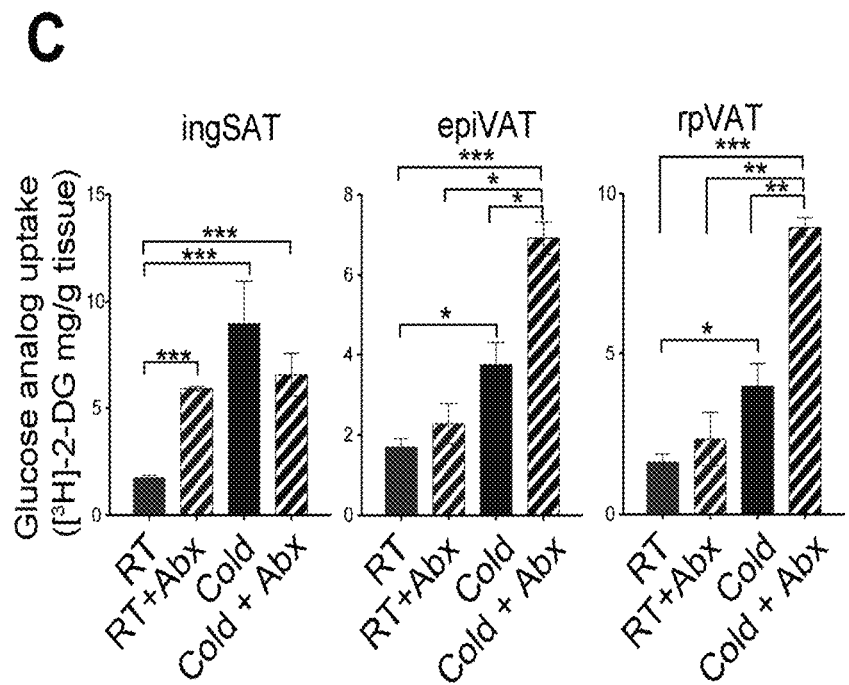

Visceral adipose tissue browning. To address the microbiota importance during long term cold exposure, we subjected antibiotics (Abx)-treated, microbiota-depleted mice to cold (referred to as "combined treatment"). Surprisingly, according to our preliminary results, not only did the mice show further improvement in their glucose tolerance compared to the nontreated- or single stimulus-treated mice, but also cold exposure of the microbiota depleted mice led to massive and preferential fat loss from the VAT (FIGS. 6A-B). While under non-stimulating conditions all treated groups showed similar increase in the SAT [$^3$H]-2-Deoxy Glucose ([$^3$H]-2-DG) glucose uptake, the VAT of the cold-exposed microbiota-depleted mice displayed markedly higher glucose uptake compared to all other groups (FIG. 6C). The dramatic VAT weight reduction despite the increased glucose uptake in this tissue in the cold-exposed microbiota-depleted mice even under basal conditions, suggest that the combined treatment causes remodelling and increase in energy dissipation, largely restricted to the visceral fat.

As shown in FIGS. 6A-C, pronounced increases of the glucose uptake in the epiVAT and rpVAT were observed in the animals following the combined treatment, together with a decrease total epiVAT and rpVAT amount. For gaining further insights into the morphological changes in epiVAT, H&E staining of epiVAT and rpVAT sections of all groups of mice were performed. Remarkably, in contrast to the control, or the single-treated cold or abx animals, the combined treatment led to approximately 40% of multilocular cells within the VAT depots (FIG. 7A). This multilocular appearance is a classical feature of beige adipocytes in vivo.

Accordingly, the visceral adipocytes from the cold-exposed microbiota-depleted mice showed increased oxygen consumption rates when compared to either RT or single treated cold-exposed mice (FIG. 7B). These data (in concert with the gene expression data shown in FIGS. 8A-E) together strongly suggest that the combined cold-exposure and microbiota-depletion leads to massive VAT remodelling and multilocular cell appearance typical for the beige fat, and that this is a phenomenon specific for the visceral adipose tissue deports of the double treated animals. These data support the idea that pronounced visceral fat browning without genetic interventions is possible, and indicate that the VAT browning can contribute to alterations in the host physiology and metabolic status.

To gain insights into the necessity of UCP1 in the visceral fat browning and remodelling, we compared groups of Ucp1-KO mice kept either at RT, cold, or following combined cold and abx treatment. Interestingly, the Ucp1-KO showed a similar response as the WT mice, where the combined treatment markedly improved glucose tolerance and promoted development of multilocular cells in the visceral fat depot of the combined cold/abx mice (FIGS. 8A-B). The gene expression profiling of the epiVAT in WT mice showed marked increase in all thermogenic markers following the combined treatment compared to the rest of the groups, with the exception of Ucp1. Specifically, while cold exposure increased the Ucp1 expression in the pg VAT of the WT mice, its levels were not different following the combined cold/abx treatment (FIG. 8C). In line with these observations and with the data from the WT mice, the Ucp1-KO animals showed similar increase in the thermogenic gene expression to the WT controls following the combined treatment, further suggesting the dispensability of UCP1 in the visceral fat browning. Without wishing to be bound by any theory, these data support the idea that the visceral multilocular adipocyte appearance and increase in the thermogenic gene expression may occur in a UCP1-independent fashion, and stress the importance of identifying the molecular mechanisms that orchestrate this process.

Identification of Bacteria with Beneficial Metabolic Effects

Figure 9:
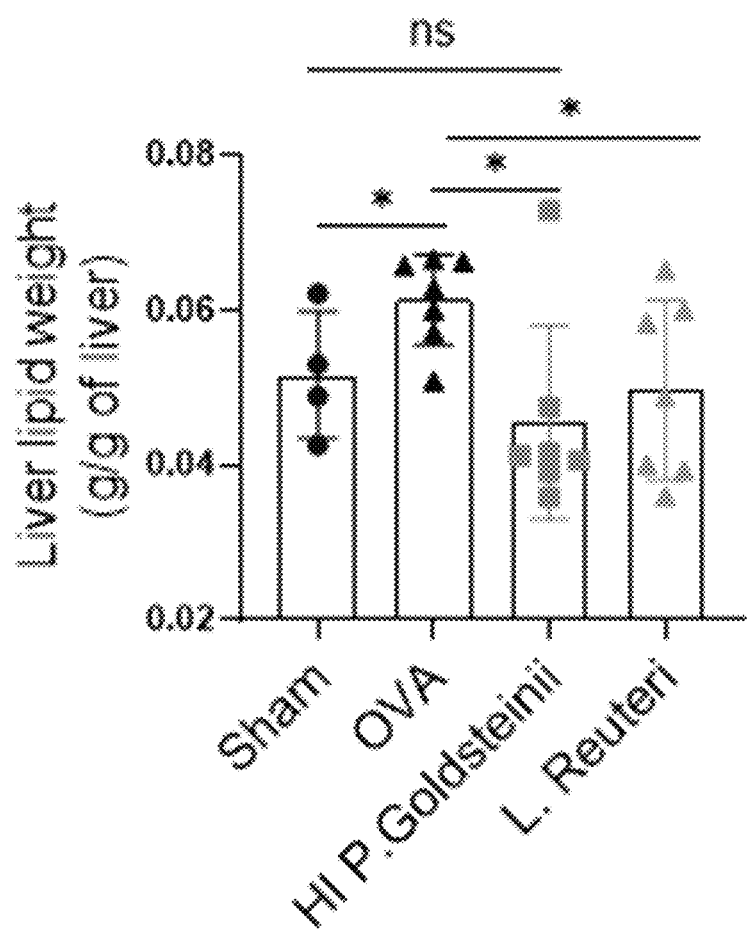
FIG. 9: Liver lipid weight in ovariectomized mice following oral supplementation of HI *Parabacteroides goldsteinii*, or *Lactobacillus reuteri* at sacrifice. Significance is calculated based on One-Way ANOVA; *P<0.05.

Using multi-omics approaches, Parabacteroides Goldsteinii was identified as consistently deregulated in various conditions which lead to improved glucose tolerance and weight reduction. Since *Parabacteroides Goldsteinii* is classified as potentially pathogenic despite being a commensal bacteria, the inventors used a heat inactivated (HI) bacterium to test the metabolic effects. Oral supplementation of the HI *Parabacteroides Goldsteinii* abolished the ovariectomy-induced liver lipid accumulation (e.g., FIG. 9). These data support the idea that this bacterium may have protective effects against fatty liver disease. In addition, it also improved the overall glycemic control, and reduced the blood glucose levels and the hyperglycemia induced by ovariectomy.

Figure 11A:
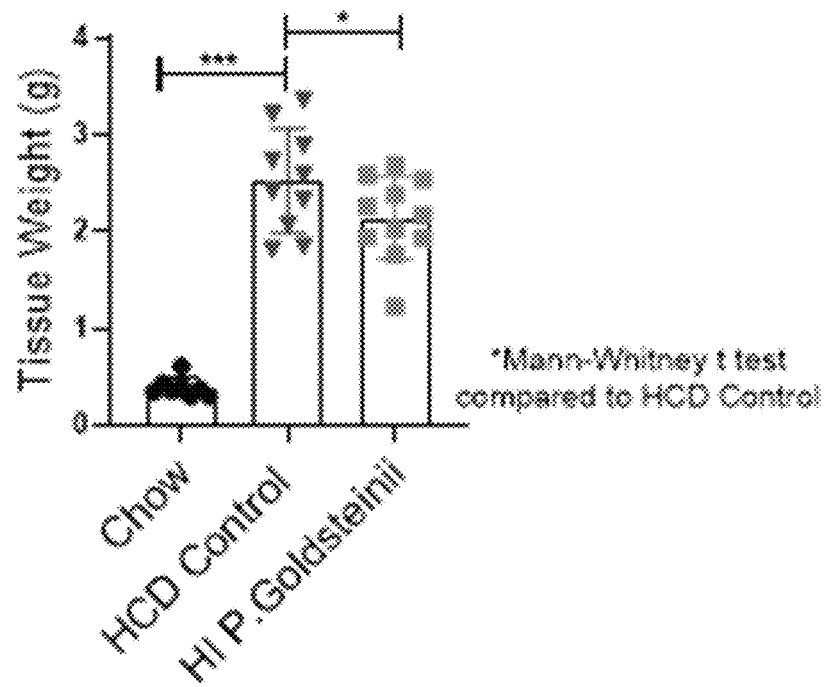
FIGS. 11A-B: Weight of subcutaneous adipose tissue (FIG. 11A), or liver (FIG. 11B) in mice fed high caloric diet for three months, followed by oral supplementation of HI Parabacteroides Goldsteinii over 4 weeks. *P<0.05, ***P<0.001.
Figure 11B:
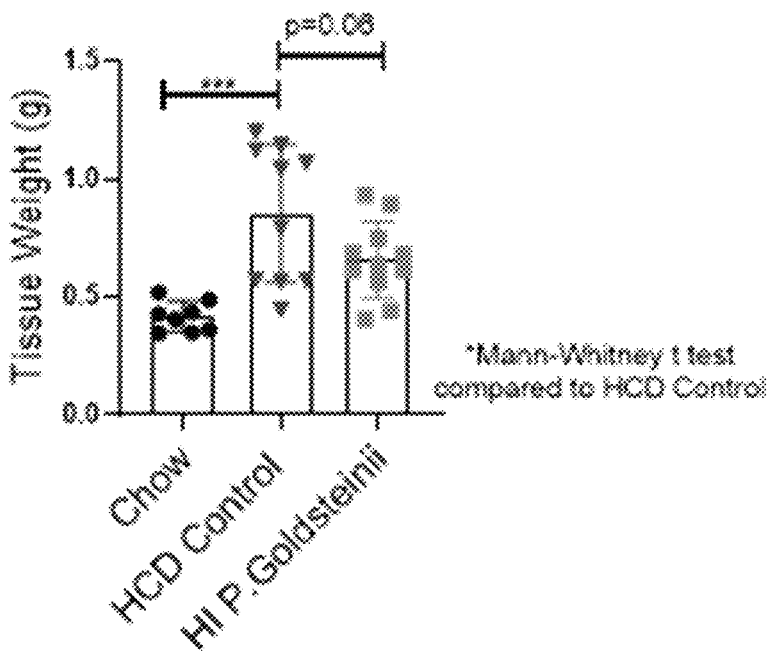

To address whether oral administration of HI *Parabacteroides Goldsteinii* can treat symptoms in vivo during diet induced obesity, the following experiments were performed. C57Bl/6 mice were fed with high caloric diet (HCD) over three months. Subsequently, mice were orally administered with HI *Parabacteroides Goldsteinii*. Body weight measurements showed that HI *Parabacteroides Goldsteinii* reduced the weight gain despite the HCD feeding to similar levels as the chow diet fed controls (FIG. 10). These effects were consistent with the reduced adipose tissue weight (FIG. 11A), and the lower liver weight that was in line with the reduced liver triglyceride content (FIG. 11 B). These results support the idea that HI *Parabacteroides Goldsteinii* can ameliorate diet induced obesity leading to weight loss and improved liver health. Full version of these data was provided to the Clayton foundation.

Polyamines Promote Growth of Beneficial Commensal Bacteria

Figure 13:
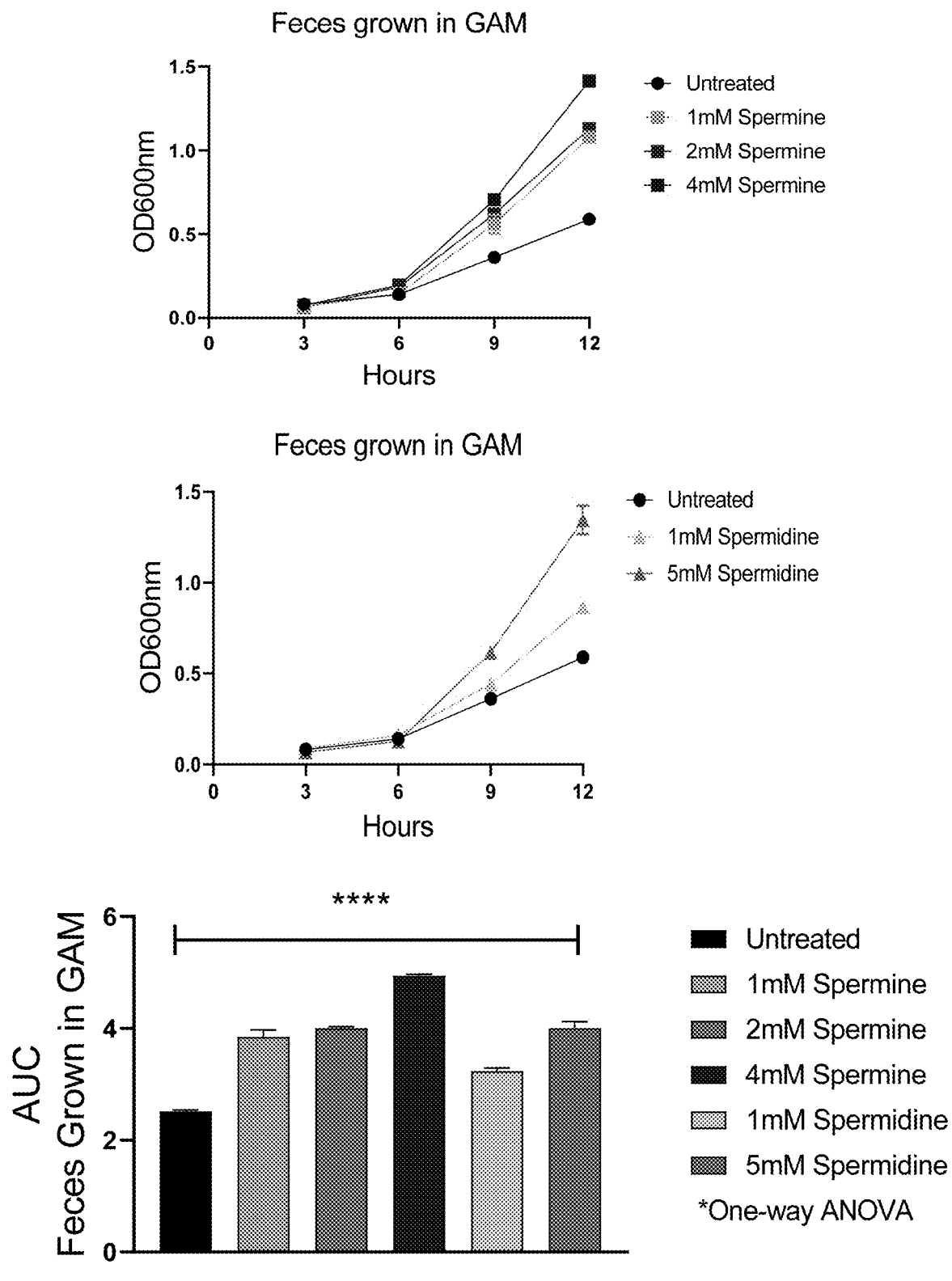
FIG. 13: Supplementation of spermine or spermidine increases growth of bacterial mix from mouse fecal samples in vitro.

The inventors next investigated whether culturing several bacteria with beneficial metabolic effects can be affected by presence of polyamines in the growth media. Both spermine and spermidine supplementation at various concentrations (FIG. 12) increased the growth of *Parabacteroides goldsteinii, Lactobacillus Reuteri* and/or *Lactobacillus Gaseri* (FIG. 12), all identified as metabolically beneficial bacteria. To further address whether the general growth of bacteria present in fresh fecal samples is affected, we inoculated fresh mouse fecal content in a growth media supplemented with various concentrations of spermine or spermidine. Both polyamines increased the optical density during the exponential growth phase (FIG. 13), showing that polyamines promote bacterial grown in a bacterial mix.

Aging has been associated with decline in the polyamine levels, and polyamine supplementation may protect against several age-related diseases, including memory impairment, cardiovascular disease, cancer, and may extend the lifespan of some organisms. To investigate whether some of these beneficial effects are to certain extent mediated by the microbiota alterations, we administered spermine and spermidine mix in vivo in mice, and transplanted the microbiota from the polyamine treated animals to ovariectomized mice. Strikingly, polyamine-adapted microbiota reduced the total fat amount owing it to a decrease in subcutaneous, visceral and brown adipose tissues. Transplantation of a control warm-adapted microbiota did not affect these parameters.

Figure 14:
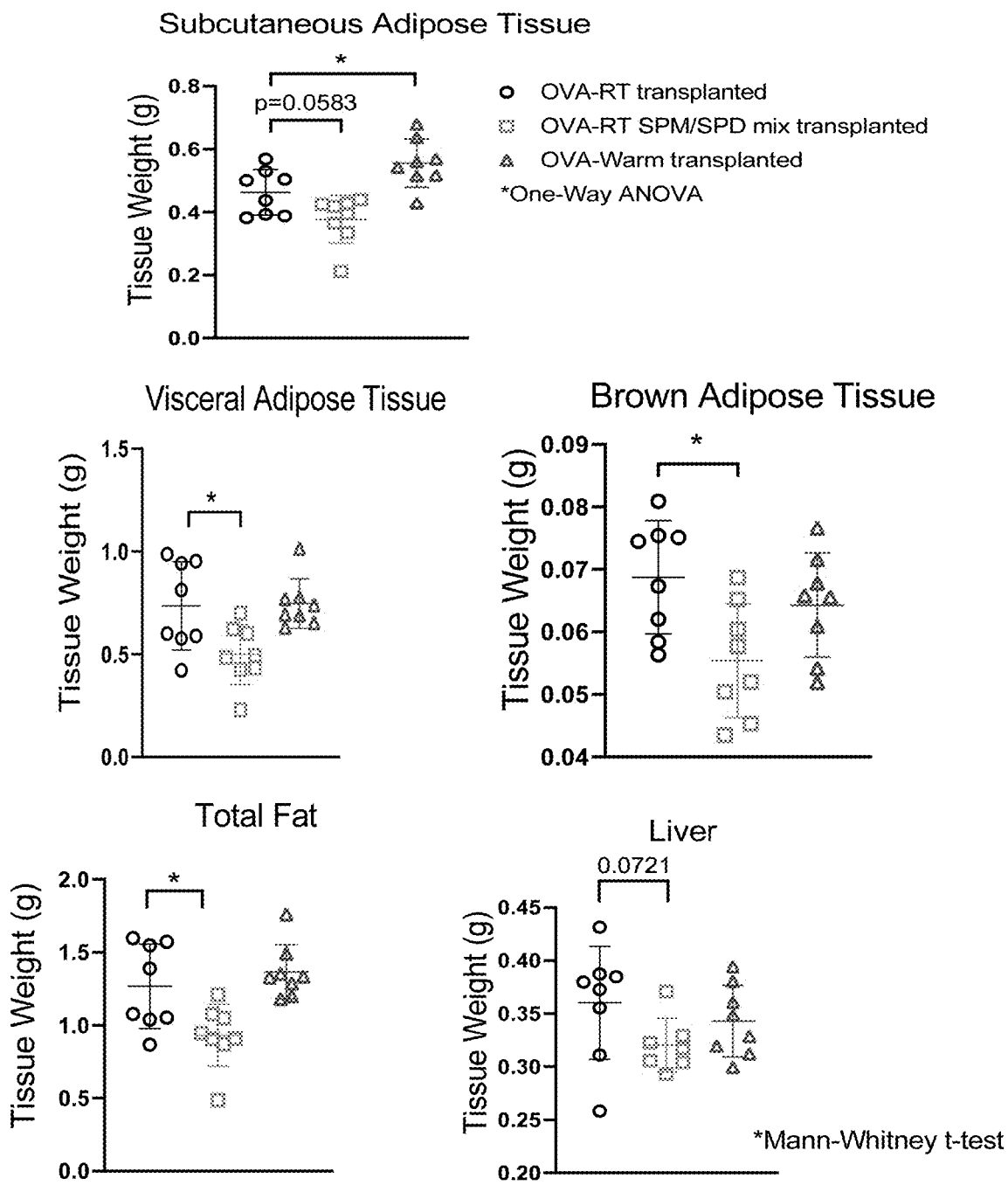
FIG. 14: Transplantation of polyamine-adapted microbiota to ovariectomized old female mice (blue) reduces weight gain by limiting adipose and liver tissue weights.

Additionally, the polyamine-adapted microbiota also reduced the total liver weight (FIG. 14). These data show that microbiota alterations induced by presence of polyamines in vivo may have beneficial metabolic effects, supporting such treatment strategies.

Example 3

Materials and Methods

Animals: All C57BL/6J mice were purchased from Janvier Labs and kept in a specific pathogen-free (SPF) facility in individually ventilated cages. All the mice were on a 12 h day/night cycle and fed a standard chow diet (16.2 MJ/kg Gross Energy; 9 kJ % Fat, 33 kJ % Protein, 58 kJ % Carbohydrates, V1534-727, Ssniff, Germany). All the mice used were either male and entered the experiment at 8 weeks of age, or female starting at 16 weeks of age (for the ovariectomy experiment). Acclimatized animals were allocated into groups based on their body weight to ensure equal starting points. Warmth exposure was done at 34° C. in a light and humidity-controlled climatic chamber (TSE, Germany) in SPF conditions using individually ventilated cages. All mice were sacrificed after 5 h fasting. All animal experiments were approved by the Swiss federal and Geneva cantonal authorities for animal experimentation (Office Vétérinaire Federal and Commission Cantonale pour les Expériences sur les animaux de Genève).

Ovariectomy: Mice were anesthetised with Xylazin/Ketamin (injection of 120 µl of a mixture of 120 mg/kg ketamine and 16 mg/kg xylazine) and shaved below the ribs on the back side. Betadine was applied to the area for appropriate disinfection. After a 1-2 cm incision through the skin and the muscle layer just below the ribs, the ovary was localized, the fallopian tube ligated with dissolving suture and the ovary removed. The muscle layer was sutured with dissolving suture, the wound closed with staples and disinfected. The same procedure was performed on the other side. A dose of Tamgesic was administered 4 hours after the surgery, and the staples were removed 7 days after the surgery under isoflurane anaesthesia. The sham-operated animals underwent the same procedure, without ligating the fallopian tube and the ovary excision.

Microbiota transplantation: For microbiota transplantation of the ovariectomized mice experiment (with a conventional microbiota already present), fecal pellets of the donors were freshly collected every 2 days and immediately homogenized in 1 ml of anaerobic PBS. After a short centrifugation (300 g, 30 sec), the supernatant was then immediately gavaged to the respective recipient. In this condition, one cage of donors (1 pellet per mouse from both mice) was used to repopulate 1 cage of recipients. Each recipient was receiving 200 µl of the donor mixture every 2 days.

Single microbe transplantation: *Lactobacillus Gasseri* (DSM 20604) and *Parabacteroides Goldsteinii* (DSM 19948) were purchased from DSMZ. *Lactobacillus reuteri* (PTA-6475) and *Akkermansia Muciniphila* (BAA835) was purchased from ATCC. *Lactobacillus Gasseri* and *Reuteri* were grown in MRS (deMan, Rogosa and Sharpe, USbiological Life Sciences, L1021-01) medium, *P. Goldsteinii* was grown in anaerobe basal broth (Thermo Scientific Oxoid Microbiology Products, CM0957), and *A. muciniphila* was grown in SCHAEDLER Broth+Vitamin K3, (Biomerieux ref 42106) in an anaerobic incubator (Coy vinyl anaerobic chamber type C) set at 37° C. with a gas mix of 5% $CO_2$, 5% H and 90% N. Freshly prepared bacteria were diluted in anaerobic PBS to a final concentration equivalent to 1 OD at 600 nm. 300 ul of this suspension was gavaged every second day to the ovariectomized mice, starting 3 days post-surgery for 2 months until the sacrifice. Gavage of the bacterial suspension to the high caloric diet (HCD) fed mice will begin either one week after starting the HCD to address the protective effects in diet induced obesity, of following three months of HCD to address the curative effects. *P. goldsteinii* preparation was heat inactivated with 100° C. for 15 min before the gavage, and the inactivation was confirmed.

Metabolic Experiments: Oral glucose tolerance tests (OGTT) were performed after 10 hr overnight fasting by oral gavage of glucose bolus (2 mg/kg body weight). Insulin tolerance test was performed after a 5 hr. fasting started in the morning, with an intraperitoneal injection of 0.5 U/kg (19278, Sigma-Aldrich). Insulin level during the OGTT was measured with the Mouse Insulin ELISA kit (ref. 10-1247-01, Mercodia), following the manufacturer's instructions.

Liver lipid measurement: Lipids from 50 mg liver were extracted with 1 ml hexane:isopropanol (3:2) by homogenising tissues in a bead-based TissueLyser equipment (Qiagen) by shaking for 30 s at 30 Hz in presence of one bead per tube. Lysates were spun at full speed in a table top centrifuge for 3 min. The supernatant was taken off. The pellet was re-extracted with 0.5 ml hexane:isopropanol, spun again and the supernatants were combined. 0.5 ml of 1 g/15 ml $Na_2SO_4$ solution was added and the tubes were mixed. The samples were spun 3 min at full speed and the upper organic phase was collected into a pre-weighed Eppendorf tube. After overnight evaporation, the tubes were weighted again and lipid weights were recorded.

Polyamines supplementation and inhibitor treatment in vivo: 6-weeks old C57BL/6J female mice were given a mixture of Spermine (Sigma-Aldrich) and Spermidine (Sigma-Aldrich) freshly dissolved in drinking water at concentration of 0.5 mM from each compound every second day during additional 45 days at room temperature. Diaminazene Acetureate (Sigma-Aldrich) was supplemented in drinking water at a concentration of 50 µm every second day during 45 days to the 16-weeks old C57BL/6J female mice that are kept at 34° C. with temperature-controlled chamber in conventional facility. Food and water were provided ad libitum.

Micro-CT analysis: Mice were/will be scanned with a micro-CT (VivaCT40/Scanco system; Zurich, Switzerland). The limbs were scanned in vivo before the ovariectomy to determine the basal state. After Xylazine/Ketamine anaesthesia, mice limbs were/will be scanned for 18 min. Final scans were/will be performed post-mortem on isolated bones. For the femoral and tibial trabecular region, we analyze one hundred slices starting from 50 slices below the distal growth plate. Femoral and tibial cortical structure was/will be assessed through 60 continuous CT slides (600 µm) from the bone midshaft. Images were/will be segmented using an adaptive-iterative threshold approach, rather than a fixed threshold. Morphometric variables were/will be computed from binarized images using direct, 3D techniques that do not rely on prior assumptions about the underlying structure. For trabecular bone regions, we assess the bone volume/total volume (BV/TV). For cortical bone at the femoral and tibial midshaft, we measure the cortical bone volume (mm3) and the average cortical thickness named cortical width (µm).

Biomechanical analysis of the bones: We use a 3-points bending test to measure biomechanical parameters of the bone. Femurs were/will be placed on two supports separated by a distance of 9.9 mm and the load was applied to the midpoint of the shaft (creating a 3-points bending). Mechanical resistance to failure (displacement and load applied) was/will be measured using a servo-controlled electromechanical system (Instron 1114, Instron corp., High Wycombe, UK) with actuator displaced at 2 mm/minute. Ultimate force (maximal load, measured in Newtons [N]), Yield point (N), stiffness (elastic energy, N/mm), and energy to fracture (surface under the curve of the plastic region, N*mm) were/will be calculated. Young's modulus (MPa) was/will be determined by the equation previously described All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alhilli and Wright, *British Journal of Experimental Pathology,* 64(1): p. 34-42, 1983.
Ashoub, M. A., *Nature,* 181(4604): p. 284, 1958.
Bray et al., Endocr Rev.; 39(2): 79-132, April 2018.
Britton et al., Journal of Cellular Physiology, 2014. 229(11): p. 1822-1830, 2014.
Calinescu et al., Eur J Pharm Biopharm., 60(1):53-60, 2005.
Chelakkot et al., Experimental & Molecular Medicine volume 50, page e450, 2018.
Chevalier et al., Cold. Cell, 163(6): p. 1360-74, 2015.
Choi et al., Sci Rep, 5: 15878, 2015.
Dar et al., Bone Rep, 8: p. 46-56, 2018.
Davis Nutr Today; 51(4): 167-174, July-August 2016.
Derrien et al., Int J Syst Evol Microbiol 2004; 54: 1469-1476.2004.
deMan et al. *USbiological Life Sciences*, L1021-01
Eisenberg et al., Nature Medicine, 14 Nov. 2016, 22(12): 1428-1438.
Ellis and Kuehn, Microbiol Mol Biol Rev., 74: 81-94, 2010.
Erttmann et al., *Nat Commun* 10:3493, 2019
Finnegan et al., Journal of Antimicrobial Chemotherapy, 65:2108-2115, 2010.
Govander et al., AAPS PharmSciTech, 15(1):29-43, 2014.
Grigoryan et al., *Journal of Hygienic Engineering and Design*, UDC 579.67:1-11.
Harland, S. C., Nature, 186(4723): p. 446-446, 1960.
Hong et al., Allergy, 66: 351-359, 2011.
Horstman and Kuehn, J Biol Chem., 277: 32538-32545, 2002.
Hussan et al., Journal of Pharmacy 2(6):5-11, 2012.
Igarashi et al., *Int J Biochem Cell Biol.,* 42(1):39-51, 2010.
Jensen et al. Circulation; 129(25 Suppl 2):S102-38; 40, Jun. 24 2014.
Kaiyala et al., Plos One, 7(8), 2012.
Kang et al., PLoS ONE, 8: e76520, 2013.
Kim et al., Clin Exp Allergy, 43: 443-454, 2013.
Kuehn and Kesty, Genes Dev., 19: 2645-2655, 2005.
Lee et al. Proteomics, 7: 3143-3153, 2007.
Lee et al., Proteomic, 9: 5425-5436, 2009.
Li, et al., Journal of Clinical Investigation, 126(6): p. 2049-2063, 2016.
Lin et al., *Microbiol Methods,* 112:3-10, 2015.
Maclean et al., *Appl Environ Microbiol,* 75(7):1932-7, 2009
Malik et al., *J. Food Eng.,* 114(3):391-396, 2013
Manas, et al., *Journal of Applied Microbiology* 98:1387-1399, 2005.
Meyer et al., Frontiers in Physiology, 8, 2017.
Million et al. Int J Obes (Lond), 36(6): 817-825, June 2012.
Morrison et al., *Neurosci Lett.,* 197(1):5-8, 1995.
Nilsson et al., J Intern Med, 2018.
Ohlsson and Sjogren, Trends Endocrinol Metab, 2015. 26(2): p. 69-74.
Soda et al., *J Immunol.,* 175(1):237-45, 2005.
Tian et al., J Biomed Res. 2010 July; 24(4):264-9
Turchanowa et al., *Eur J Clin Invest.* 30(1):72-8, 2000.
Vernon et al., Aliment Pharmacol Ther.; 34(3):274-85, August 2011.
Wallia et al., JAMA.; 311(22):2315-25, Jun. 11 2014.
World Health Organ Tech Rep Ser.; 8940:i-xii, 1-253; PMID: 11234459, 2000.
Wu et al., *Hirsutella sinensis,* Gut. 68(2):248-262, 2019.
Yamamoto et al., *Br J Pharmacol.,* 166(3): 1084-1096, 2012.
Yang et al., 235(1-2):1-15, 2002.

What is claimed is:

1. A method for treating a metabolic disease or disorder in a mammalian subject, comprising administering a composition to the gastrointestinal system of the subject, wherein the composition comprises the therapeutically effective amount of inactivated *Parabacteroides goldsteinii*.

2. The method of claim 1, wherein the inactivated *Parabacteroides goldsteinii* is heat-inactivated.

3. The method of claim 1, wherein the inactivated *Parabacteroides goldsteinii* has been inactivated via exposure to a peroxide.

4. The method of claim 3, wherein the peroxide is hydrogen peroxide.

5. The method of claim 3, wherein the peroxide is hydrogen peroxide vapor.

6. The method of claim 1, wherein the inactivated *Parabacteroides goldsteinii* has been inactivated via exposure to radiation or ionizing radiation.

7. The method of claim 6, wherein the radiation comprises or consists of light having a wavelength of about 400-420 nm.

8. The method of claim 1, wherein the inactivated *Parabacteroides goldsteinii* has been inactivated via exposure to air plasma, ultrasound under pressure, an alcohol, high hydrostatic pressure (HHP), or pulsed electric field (PEF).

9. The method of claim 8, wherein the alcohol is ethanol.

10. The method of claim 1, wherein the composition comprises from about $1 \times 10^8$ to about $1 \times 10^{13}$ colony forming units (cfu) of the inactivated *Parabacteroides goldsteinii*.

11. The method of claim 1, wherein the composition further comprises *Lactobacillus gasseri, Lactobacillus reuteri*, or *Akkermansia muciniphila*.

12. The method of claim 1, wherein the composition is further defined as a pharmaceutical composition.

13. The method of claim 1, wherein the composition is further defined as a probiotic composition.

14. The method of claim 1, wherein the composition further comprises *Lactobacillus gasseri* or *Lactobacillus* reuteri.

15. The method of claim 1, wherein the composition further comprises extracellular vesicles from *Lactobacillus gasseri* or *Lactobacillus* reuteri.

16. The method of claim 1, wherein the composition is administered orally, colonically, via enema, via an orogastric tube, or via a nasogastric tube.

17. The method of claim 1, wherein the composition is further defined as a pharmaceutical or probiotic composition that is resistant to degradation in the stomach but releases bacteria in the small intestine and/or large intestine of the subject.

18. The method of claim 1, wherein the composition comprises an enteric coating, chitosan-alginate beads, or a hydrogel.

19. The method of claim 18, wherein the enteric coating is a fatty acid, a wax, a shellac, a plastic, a phthalate, cellulose acetate phthalate (CAP), Cellulose acetate trimellitate (CAT), Poly(vinyl acetate phthlate) (PVAP), hydroxypropyl methylcellulose phthalate (HPMCP), or a plant fiber.

20. The method of claim 1, wherein the composition does not comprise an enteric coating.

21. The method of claim 1, wherein the composition is a tablet or capsule.

22. The method of claim 1, wherein the subject is a human.

23. The method of claim 22, wherein the human is a postmenopausal woman.

24. The method of claim 1, wherein the metabolic disease or disorder is obesity, type 2 diabetes, fatty liver disease, insulin resistance, or dyslipidemia.

25. The method of claim 24, wherein the fatty liver disease is nonalcoholic fatty liver disease (NAFLD).

26. The method of claim 1, wherein the inactivated Parabacteriodes goldsteinii in the composition has been purified or cultured.

27. The method of claim 1, wherein the *Parabacteroides goldsteinii* has been inactivated by heating to about 95-105° C. for about 10-20 min.

28. The method of claim 27, wherein the *Parabacteroides goldsteinii* has been inactivated by heating to about 100° C. for about 15 min.

29. The method of claim 1, wherein the method further comprises enterically administering spermine and/or spermidine to the subject.

30. The method of claim 29, wherein the method comprises enterically administering both spermine and spermidine to the subject.

31. The method of claim 29, wherein the method comprises administering about 1-50 mg per kg body weight per day spermine to the subject.

32. The method of claim 29, wherein the method comprises administering about 1-50 mg per kg body weight per day spermidine to the subject.

33. The method of claim 1, wherein the composition comprises the spermine and/or spermidine.

34. The method of claim 33, wherein the composition comprises both spermine and spermidine.

35. The method of claim 1, wherein the inactivated *Parabacteroides goldsteinii* is cultured or expanded in a medium comprising spermidine or spermine.

36. The method of claim 35, wherein the medium comprises about 0.1-6 mM spermidine.

37. The method of claim 35, wherein the medium comprises about 0.1-6 mM spermine.

\* \* \* \* \*

UNITED STATES PATENT AND TRADEMARK OFFICE
CERTIFICATE OF CORRECTION

| | |
|---|---|
| PATENT NO. | : 11,883,447 B2 |
| APPLICATION NO. | : 17/025811 |
| DATED | : January 30, 2024 |
| INVENTOR(S) | : Mirko Trajkovski et al. |

It is certified that error appears in the above-identified patent and that said Letters Patent is hereby corrected as shown below:

In the Claims

Claim 14, Column 26, Line 37, "reuteri" should be --*reuteri*--.

Claim 15, Column 26, Line 40, "reuteri" should be --*reuteri*--.

Claim 26, Column 27, Line 4, "Parabacteroides goldsteinii" should be --*Parabacteroides goldsteinii*--.

Signed and Sealed this
Twenty-seventh Day of August, 2024

Katherine Kelly Vidal
*Director of the United States Patent and Trademark Office*